US008469872B2

(12) United States Patent
Sotiriou

(10) Patent No.: US 8,469,872 B2
(45) Date of Patent: Jun. 25, 2013

(54) MAGNETIC THERAPY DEVICE

(76) Inventor: George Sotiriou, Farmingville, NY (US)

(*) Notice: Subject to any disclaimer, the term of this patent is extended or adjusted under 35 U.S.C. 154(b) by 783 days.

(21) Appl. No.: 12/631,180

(22) Filed: Dec. 4, 2009

(65) Prior Publication Data
US 2010/0081858 A1 Apr. 1, 2010

Related U.S. Application Data

(63) Continuation-in-part of application No. 11/247,365, filed on Oct. 11, 2005, now Pat. No. 7,648,454, and a continuation-in-part of application No. 11/875,452, filed on Oct. 19, 2007, now Pat. No. 7,915,846, and a continuation-in-part of application No. 11/875,459, filed on Oct. 19, 2007, now Pat. No. 8,021,292, and a continuation-in-part of application No. 11/875,465, filed on Oct. 19, 2007, now Pat. No. 7,803,104, and a continuation-in-part of application No. 11/875,477, filed on Oct. 19, 2007, now Pat. No. 8,257,242.

(51) Int. Cl.
A61N 2/00 (2006.01)

(52) U.S. Cl.
USPC .......................................................... 600/9

(58) Field of Classification Search
USPC ....................................................... 600/9–15
See application file for complete search history.

(56) References Cited

U.S. PATENT DOCUMENTS

| 3,821,509 | A |   | 6/1974  | Amagami et al. |
| 3,887,781 | A |   | 6/1975  | Peters, Jr. |
| 4,228,387 | A |   | 10/1980 | Brown |
| 4,340,890 | A |   | 7/1982  | Fritze |
| 4,350,937 | A |   | 9/1982  | Miyazaki et al. |
| 4,455,516 | A | * | 6/1984  | Furusho ............ 318/400.41 |
| 4,537,181 | A |   | 8/1985  | Shalhoob et al. |
| 4,584,994 | A | * | 4/1986  | Bamberger et al. ......... 600/40 |
| 4,727,857 | A |   | 3/1988  | Horl |
| 5,632,720 | A |   | 5/1997  | Kleitz |
| 5,667,469 | A |   | 9/1997  | Zhang et al. |
| 5,762,599 | A |   | 6/1998  | Sohn |
| 6,001,055 | A |   | 12/1999 | Souder |

(Continued)

OTHER PUBLICATIONS

Non-Final Office Action for U.S. Appl. No. 11/875,465, mailed Aug. 5, 2009, 14 pages.

(Continued)

Primary Examiner — Samuel Gilbert
(74) Attorney, Agent, or Firm — Brake Hughes Bellermann LLP; Shane A. Kennedy

(57) ABSTRACT

A magnetic therapy device may include a housing, a disk, a tachometer, a microprocessor, a driver integrated circuit, and a plurality of coils. The disk may include a plurality of magnets thereon, the disk being mounted inside the housing and configured to rotate within the housing. The tachometer may be configured to monitor a magnetic field generated by the plurality of magnets and provide a frequency signal to a microprocessor based on the monitored magnetic field. The microprocessor may be configured to provide a control signal to the driver integrated circuit based on the frequency signal, the microprocessor being programmed to provide the control signal to maintain a constant speed of rotation of the disk based on the frequency signal. The driver integrated circuit may be configured to provide a current to a plurality of coils based on the control signal. The plurality of coils may be configured to generate, based on the current received from the driver integrated circuit, a magnetic field which will generate a force on the plurality of magnets and thereby cause the disk to rotate.

18 Claims, 19 Drawing Sheets

U.S. PATENT DOCUMENTS

| | | | |
|---|---|---|---|
| 6,065,210 | A | 5/2000 | Bove |
| 6,092,531 | A | 7/2000 | Chen et al. |
| 6,123,657 | A | 9/2000 | Ishikawa et al. |
| 6,155,966 | A | 12/2000 | Parker |
| 6,231,497 | B1 | 5/2001 | Souder |
| 6,238,333 | B1 | 5/2001 | Loos et al. |
| 6,245,006 | B1 | 6/2001 | Olson |
| 6,265,984 | B1 | 7/2001 | Molinaroli |
| 6,461,377 | B1 | 10/2002 | An |
| 6,496,389 | B1 | 12/2002 | Yasumura |
| 6,626,818 | B2 | 9/2003 | Sexton |
| 6,648,812 | B2 | 11/2003 | Ardizzone |
| 6,663,557 | B2 | 12/2003 | Werny |
| 6,679,825 | B2 | 1/2004 | Alicea |
| 6,781,697 | B1 | 8/2004 | Carra et al. |
| 7,130,201 | B2 | 10/2006 | Yao |
| 7,485,993 | B2 * | 2/2009 | Huang et al. ............ 310/81 |
| 7,648,454 | B2 | 1/2010 | Sotiriou |
| 7,803,104 | B2 | 9/2010 | Sotiriou |
| 7,915,846 | B2 | 3/2011 | Sotiriou |
| 8,021,292 | B2 | 9/2011 | Sotiriou |
| 8,050,059 | B2 | 11/2011 | Sotiriou |
| 8,257,242 | B2 * | 9/2012 | Sotiriou ..................... 600/9 |
| 2002/0147380 | A1 | 10/2002 | Ardizzone |
| 2004/0122281 | A1 | 6/2004 | Fischell et al. |
| 2004/0150372 | A1 | 8/2004 | Lee et al. |
| 2005/0034902 | A1 | 2/2005 | Madhavarao et al. |
| 2009/0102587 | A1 | 4/2009 | Sotiriou |
| 2009/0103332 | A1 | 4/2009 | Sotiriou |
| 2009/0105519 | A1 | 4/2009 | Sotiriou |
| 2009/0105520 | A1 | 4/2009 | Sotiriou |
| 2010/0085777 | A1 | 4/2010 | Sotiriou |

OTHER PUBLICATIONS

Final Office Action for U.S. Appl. No. 11/247,365, mailed Jul. 13, 2009, 11 pages.
Non-Final Office Action for U.S. Appl. No. 11/247,365, mailed Feb. 24, 2009, 11 pages.
Final Office Action for U.S. Appl. No. 11/247,365, mailed Apr. 30, 2008, 11 pages.
Non-Final Office Action for U.S. Appl. No. 11/247,365, mailed Oct. 18, 2007, 5 pages.
Non-Final Office Action for U.S. Appl. No. 11/875,452, mailed Nov. 30, 2009, 10 pages.
Office Action received for U.S. Appl. No. 11/875,465, mailed on Feb. 5, 2010, 17 pages.
Non-Final Office Action for U.S. Appl. No. 11/875,452, mailed on Jun. 11, 2010, 18 pages.
Notice of Allowance received for U.S. Appl. No. 11/875,452, mailed on Dec. 13, 2010, 8 pages.
Response to Notice of Allowance filed for U.S. Appl. No. 11/875,459, filed Jun. 6, 2011, 6 pages.
Notice of Allowance received for U.S. Appl. No. 11/875,459, mailed on Apr. 1, 2011, 18 pages.
Notice of Allowance received for U.S. Appl. No. 11/875,465, mailed on Aug. 18, 2010, 7 pages.
Response to Non-Final Office Action filed for U.S. Appl. No. 11/875,477, filed Jul. 1, 2011, 10 pages.
Response to Non-Final Office Action filed for U.S. Appl. No. 11/875,477, filed Jan. 19, 2012, 2 pages.
Non-Final Office Action received for U.S. Appl. No. 11/875,477, mailed on Apr. 1, 2011, 17 pages.
Non-Final Office Action received for U.S. Appl. No. 11/875,477, mailed on Oct. 19, 2011, 12 pages.
Notice of Allowance received for U.S. Appl. No. 11/875,477, mailed on Jun. 29, 2012, 8 pages.
Notice of Allowance received for U.S. Appl. No. 12/633,564, mailed on Jul. 29, 2011, 5 pages.
Response to Final Office Action filed for U.S. Appl. No. 12/633,564, filed Jun. 28, 2011, 7 pages.
Final Office Action received for U.S. Appl. No. 12/633,564, mailed on Apr. 28, 2011, 10 pages.
Non-Final Office Action received for U.S. Appl. No. 12/633,564, mailed on Dec. 2, 2010, 19 pages.
Response to Non-Final Office Action filed for U.S. Appl. No. 12/633,564, filed Feb. 9, 2011, 11 pages.

* cited by examiner

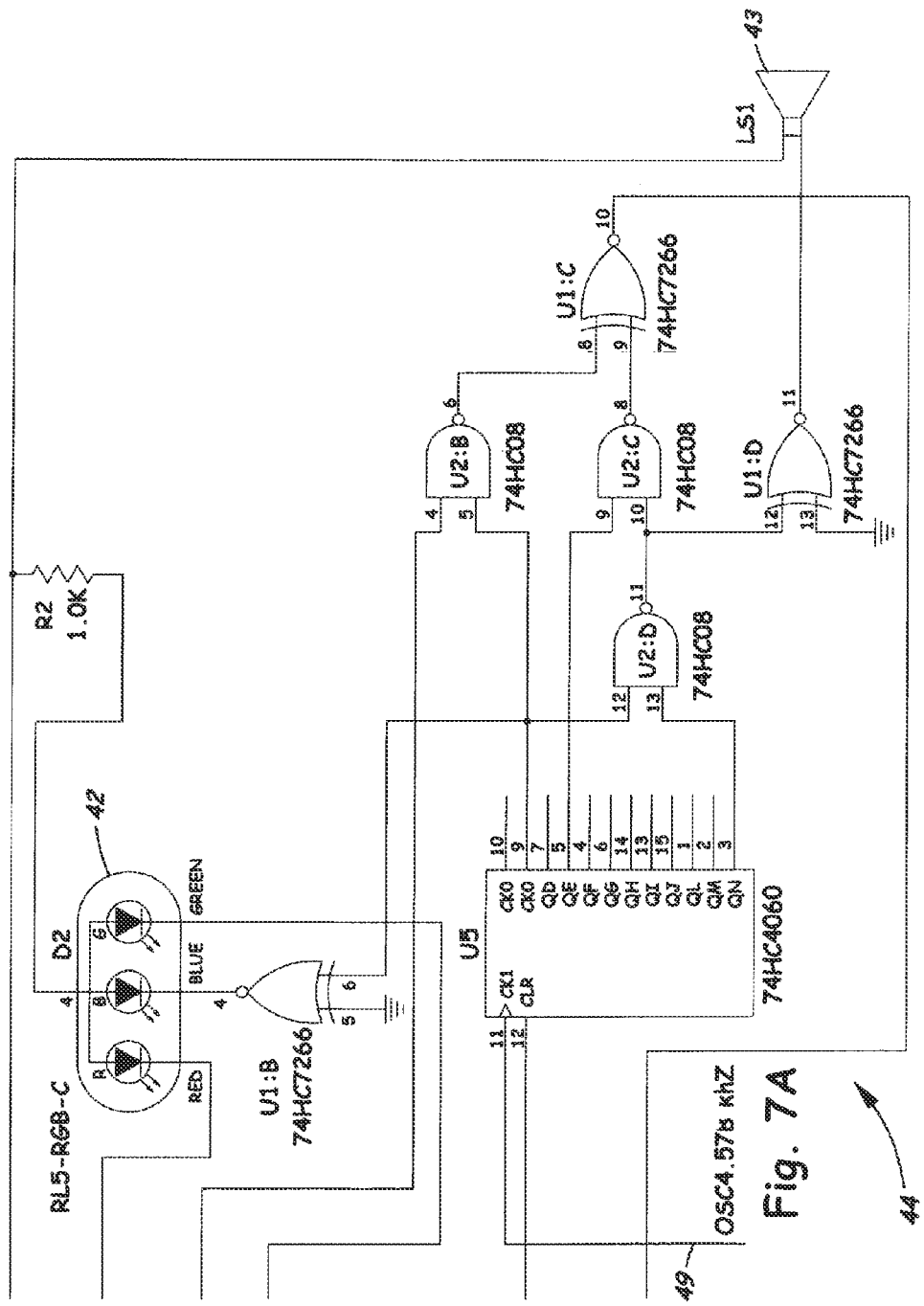

LI-ION BATTERY CHARGER

MAGNETIC THERAPY DEVICE

CROSS-REFERENCE TO RELATED APPLICATIONS

This application is a continuation-in-part application, and claims priority from, U.S. patent application Ser. No. 11/247,365, filed on Oct. 11, 2005, entitled "Magnetic Therapy Device," U.S. patent application Ser. No. 11/875,452, filed on Oct. 19, 2007, entitled "Charging Probe Circuit," U.S. patent application Ser. No. 11/875,459, filed on Oct. 19, 2007, entitled "Magnetic Therapy Device," U.S. patent application Ser. No. 11/875,465, filed on Oct. 19, 2007, entitled "Magnetic Therapy Device," and U.S. patent application Ser. No. 11/875,477, filed on Oct. 19, 2007, entitled "Magnetic Therapy Device," the disclosures of all of which are incorporated herein by reference in their entirety.

TECHNICAL FIELD

This description relates to electrical circuits.

BACKGROUND

Magnetic therapy has been found to have therapeutic effect on humans. Subjecting parts of the human body to magnetic fields may have beneficial effects.

SUMMARY

According to one general aspect, a magnetic therapy device may include a housing, a disk, a tachometer, a microprocessor, a driver integrated circuit, and a plurality of coils. The disk may include a plurality of magnets thereon, the disk being mounted inside the housing and configured to rotate within the housing. The tachometer may be configured to monitor a magnetic field generated by the plurality of magnets and provide a frequency signal to a microprocessor based on the monitored magnetic field. The microprocessor may be configured to provide a control signal to the driver integrated circuit based on the frequency signal, the microprocessor being programmed to provide the control signal to maintain a constant speed of rotation of the disk based on the frequency signal. The driver integrated circuit may be configured to provide a current to a plurality of coils based on the control signal. The plurality of coils may be configured to generate, based on the current received from the driver integrated circuit, a magnetic field which will generate a force on the plurality of magnets and thereby cause the disk to rotate.

According to another general aspect, magnetic therapy device comprising may include a housing, a motor, a disk, a receiver coil, and a circuit. The motor may be mounted on the housing and configured to cause the disk to spin when the motor is active and receive power from a battery. The disk may be mounted on the motor, and may have a plurality of magnets mounted on the disk. The receiver coil may be configured to receive power from a magnetic field and transfer the power to the battery. The circuit may be configured to cause the motor to become active for a finite duration of time and then become inactive before the battery has been drained of power, and to cause the motor to become active when an inductive probe is taken away from the receiver coil.

The details of one or more implementations are set forth in the accompanying drawings and the description below. Other features will be apparent from the description and drawings, and from the claims.

BRIEF DESCRIPTION OF THE DRAWINGS

FIGS. 7A and 7B are circuit diagrams showing the preferred embodiment of the circuit for the sequential controller, which determines when the therapy cycle begins and ends and controls the tri-state LED indicator.

DETAILED DESCRIPTION

Figure 1:
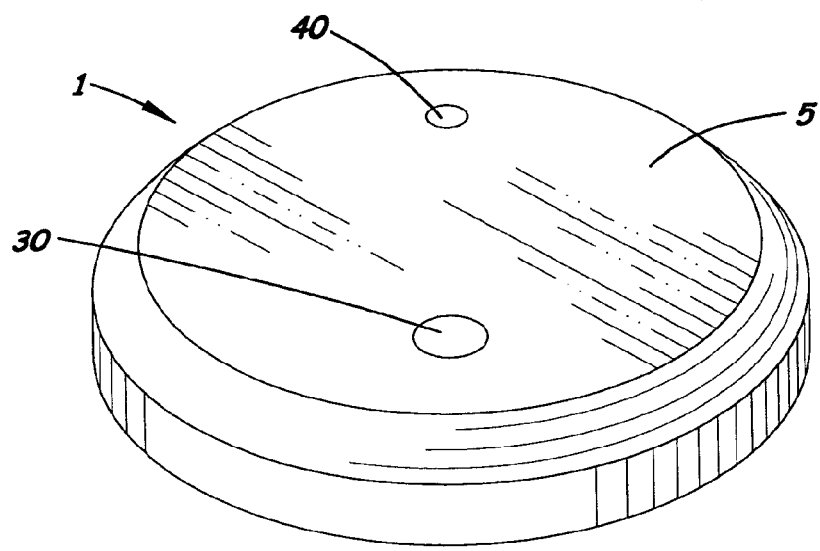
FIG. 1 shows a perspective view of the preferred embodiment of the magnetic therapy device, with the housing, probe insertion hole, and tri-state LED visible.
Figure 2:
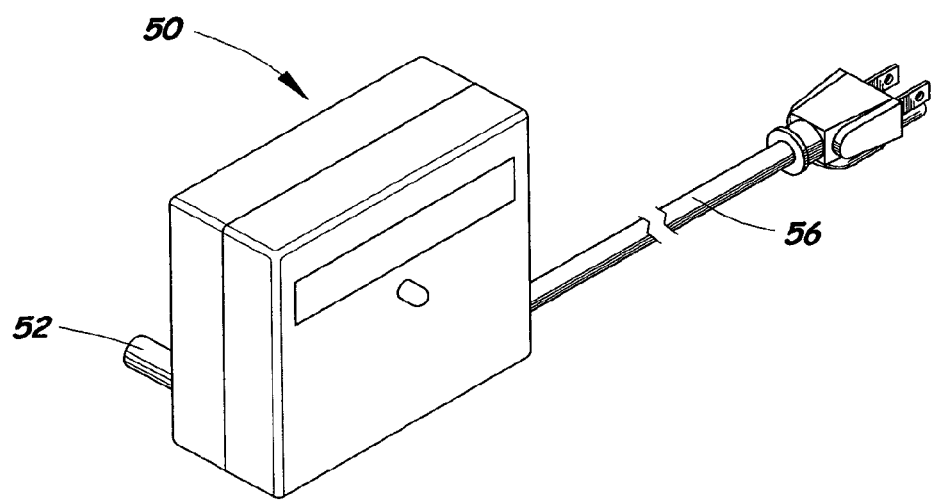
FIG. 2 shows a perspective view of the preferred embodiment of the inductive charging probe.

One embodiment of the magnetic therapy device 1 is comprised of four elements: (1) a magnetic field generator, which is comprised of a disk 10 with magnets 12 mounted thereon which, when rotating, generates a dynamic magnetic field; (2) a magnetic frequency generator, which comprises a DC motor 20 controlled by a magnetic field generator circuit 22 which controls the rotational speed of the DC motor; (3) the sequential logic controller circuit 44, which controls the therapy cycle and the tri-state LED 42 which indicates the status of the therapy cycle and the rechargeable battery 36; and (4) a rechargeable battery 36 which is part of the battery charging circuit 34 which enables the battery 36 to be recharged without any electrical contacts. An inductive probe 50 is used to recharge the battery 36 without any electrical contacts. In this embodiment, the four elements of the magnetic therapy device 1 are made entirely of non-magnetic material, except for the magnets 12 and motor 20, because any magnetic material within close proximity of the magnets 12 would create a magnetic drag, requiring more power to the motor 20 to maintain the rotational speed of the disk 10, reducing the efficiency of the device.

In one embodiment, the four elements of the single magnetic therapy device 1, which comprises a single rotating disk 10, are contained in a single housing 5 which is completely sealed and water proof, enabling the device to be used in a bathtub during therapy and handwashed, if desired; only the probe insertion hole 30 and the tri-state LED 40 are visible from the outside. The device is four inches in diameter and ¾ inches thick and disk-shaped in this embodiment, approximately the size and shape of a hockey puck. This embodiment of the device is round and dark gray, and resembles a smooth river stone. This small size allows it to be easily held in one hand and used to massage or otherwise contact a user's body during magnetic therapy. It is believed that the device could be up to eight inches in diameter and two inches thick and still have this advantage. The self-controlled therapy cycle described below also makes the device easy to use. The small size, portability, and hand-held nature of the magnetic therapy device enable the magnetic therapy device to be used without any parts outside the disk-shaped housing 5, such as a stand, seat, or handles, once the battery 36 has been sufficiently charged.

Figure 3A:
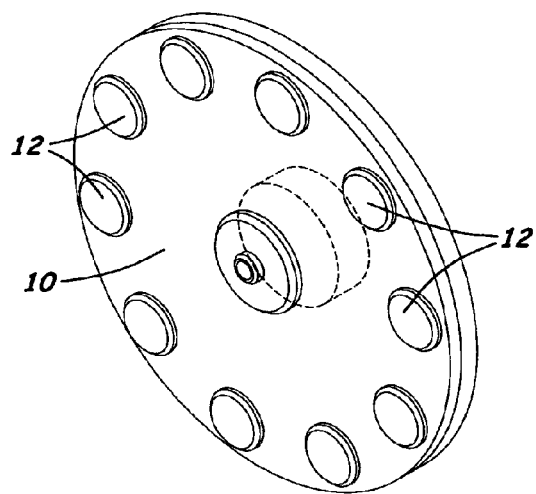
FIG. 3a shows a side perspective view of the preferred embodiment of the disk with ten rare earth magnets mounted on the top surface of the disk in a circular pattern with equal spacing.
Figure 3B:
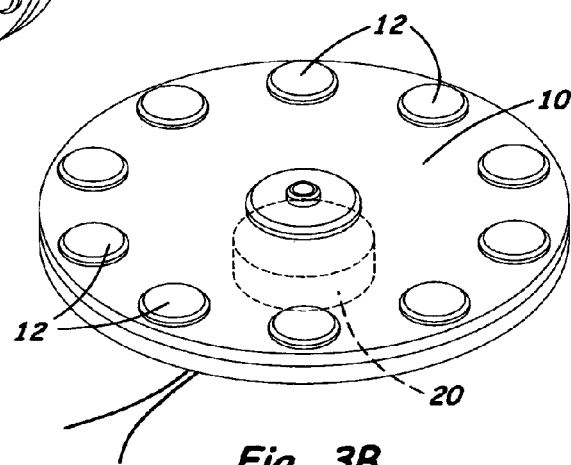
FIG. 3b shows a top perspective view of the preferred embodiment of the disk with ten rare earth magnets mounted on the top surface of the disk in a circular pattern with equal spacing, and also shows the motor attached to the disk.
Figure 4:
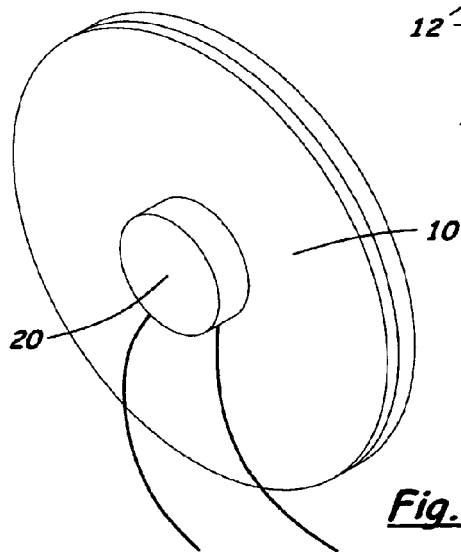
FIG. 4 shows a bottom perspective view of the preferred embodiment of the disk and shows the motor attached to the disk.

The magnetic field generator, shown in FIGS. 3a, 3b, and 4, begins with the disk 10. In one embodiment, the disk 10 is three inches in diameter and less than half an inch thick. The disk is made of a non-magnetic material, such as plastic or fiberglass FR-4. Magnets 12 are mounted on the top surface of the disk 10 by means of a press fit or by epoxy in a circular pattern with even spacing and alternating polarities. The alternating polarities of the magnets 12 creates a dynamic, sinusoidal magnetic field when the disk 10 spins. The device will function to create a dynamic or changing magnetic field as long as at least one magnet 12 is mounted on the disk 10; however, the more magnets 12 are mounted on the disk 10, the higher the frequency of the magnetic field. In one embodiment, ten rare earth magnets 12, namely neodymium magnets, are mounted on the disk 10. Neodymium magnets are a member of the Rare Earth magnet family and are the most powerful permanent magnets in the world. They are also referred to as NdFeB magnets, or NIB, because they are composed mainly of Neodymium (Nd), Iron (Fe) and Boron (B). The neodymium magnets 12 used in this embodiment are circular, ⅜ inches in diameter, and 3⁄16 inches thick. These neodymium magnets 12 generate a magnetic field strength of 100,000 Gauss when the disk 10 is spinning in this embodiment.

The use of a disk 10 ("disk" being defined as an object that is generally circular, has generally even thickness, and has a diameter greater than its thickness), which is contained inside the accompanying housing 12, which is also disk-shaped as previously defined in this sentence, enables the device to have all of the magnets 12 near the user's body, allowing for good depth penetration of the magnetic field into the user's body. The use of a disk 10 with the magnets 12 mounted on the top surface of the disk 10 also allows all magnetic poles to be equidistant from the user's body, which creates a more therapeutic magnetic field. The equal spacing of the magnets 12 in a circular pattern with alternating polarities allows the magnetic field to vary in a sinusoidal manner.

The disk 10 is secured to the shaft of a DC motor 20; in one embodiment, the means of securement is epoxy. Because the shaft is considered part of the DC motor 20, the disk 10 may be considered to be "mounted" on the DC motor 20. The DC motor 20 causes the disk 10 to rotate on an axis passing through the center of the disk which is perpendicular to the top and bottom surfaces of the disk 10, creating the dynamic magnetic field. By mounting the disk 10 onto a small DC motor 20, the magnetic therapy device can be manufactured with a disk-shaped housing 5 with no need for pulleys, resulting in a smaller and more efficient device. The DC motor 20 is connected (directly or indirectly) to the housing 5, and contained entirely within the housing 5. In one embodiment, the DC motor 20 is mounted to an electronic component circuit board, and the electronic component circuit board is secured to the housing 5. A DC motor 20 is used so that the device can be powered by a battery 36 and easily handled rather than needing to be attached to a cord which is plugged into a wall. In the embodiment described herein, the battery 36 is rechargeable; non-rechargeable batteries could also be used, but would require the housing 5 to be unsealed to replace the batteries when they run out.

The motor 20 has varying rotational speeds to allow the strength and frequency of the magnetic field to be varied. The relationship between the frequency of the magnetic field and the rotational speed of the disk 10 is $f = n \times rpm/120$, where f is the frequency of the magnetic field, n is the number of magnetic poles or magnets 12, and rpm is the number of revolutions per minute of the disk 10.

Figure 5A:
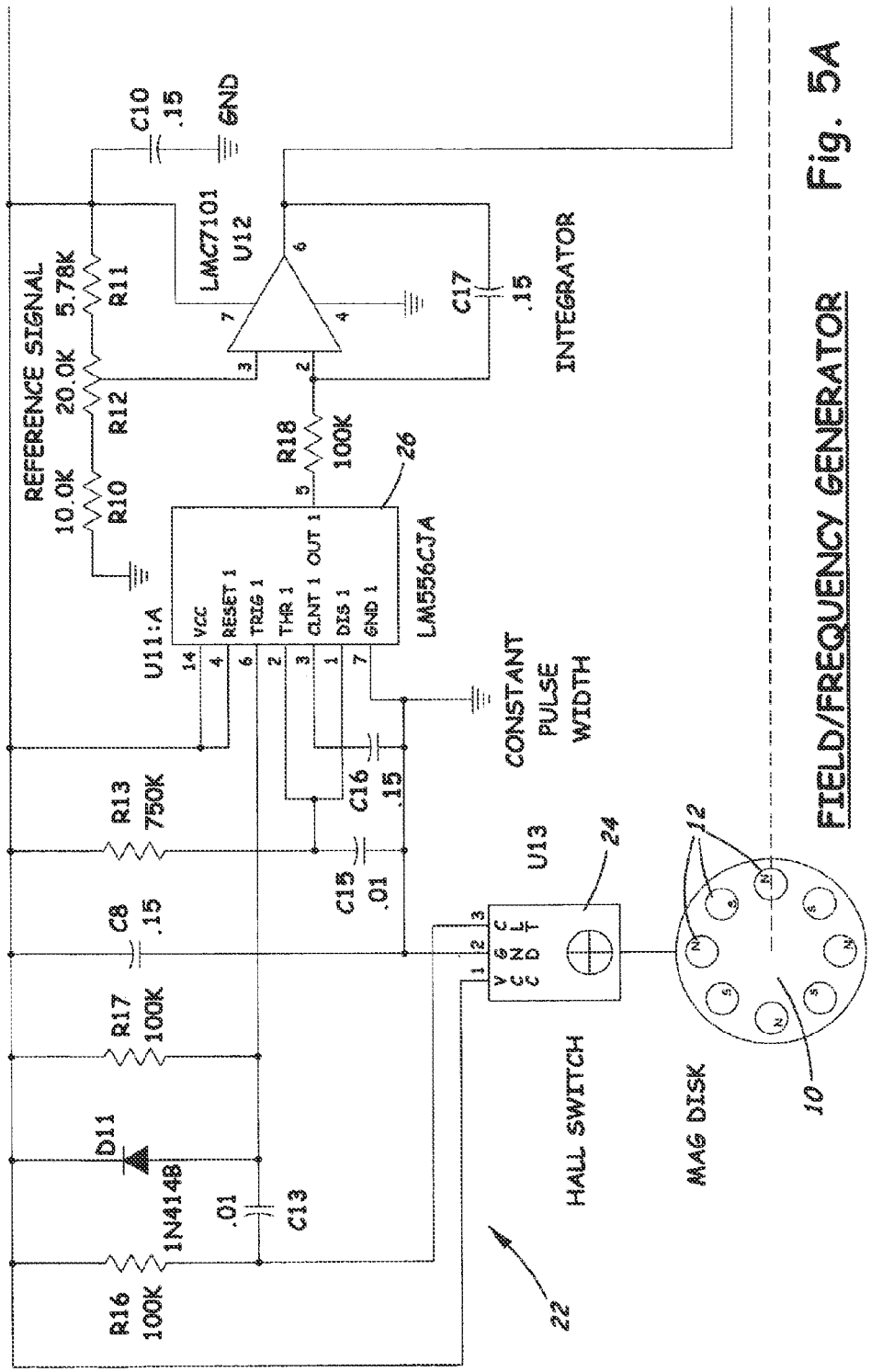
FIGS. 5A and 5B are circuit diagrams showing an embodiment of the magnetic field generator circuit that determines the magnetic field frequency by controlling the rotational speed of the DC motor.
Figure 5B:
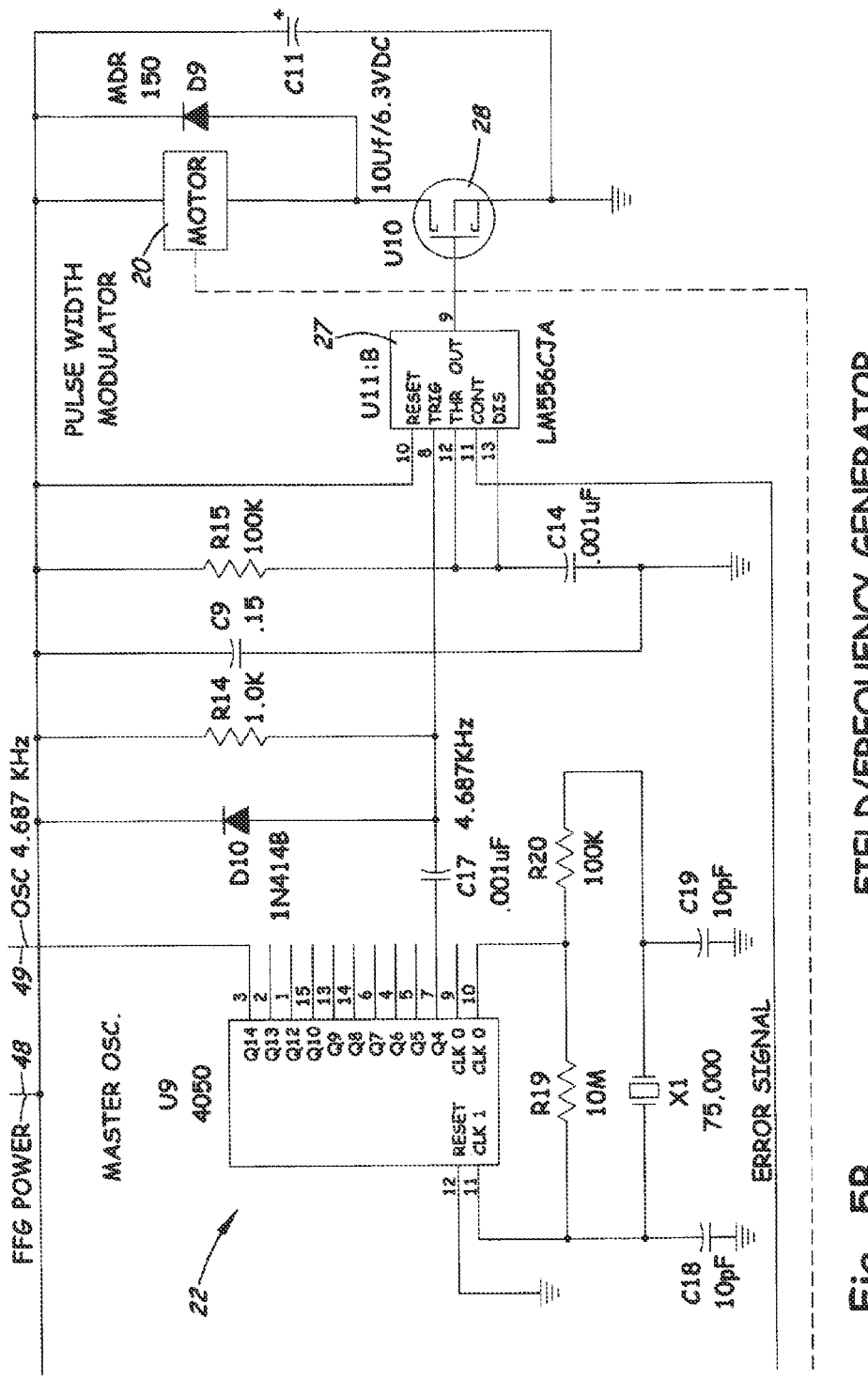

The magnetic frequency generator circuit 22 controlling the motor 20 could take on different designs depending on the type of motor 20, which could be a brush type, brushless type, or stepper type, among others. One embodiment uses a brush type motor 20 because it is relatively inexpensive and efficient in terms of power versus torque; the circuitry 22 used in this embodiment is shown in FIGS. 5A and 5B. The magnetic frequency generator circuit 22 of this embodiment receives two inputs from the sequential controller circuit 44: (1) field frequency generator power 48, and (2) oscillation frequency 49, which, in this embodiment, is 4.687 kHz. A latching hall effect switch 24 creates a feedback path for the motor 20. The latching hall effect switch 24 also generates a pulse for each cycle of the sinusoidal magnetic wave. The pulse triggers a first monostable multivibrator 26; the output of the first monostable multivibrator 26 is a precise pulse width which remains constant regardless of the rotational speed of the disk 10. This precise output pulse of the first monostable multivibrator 26 is fed into an operational amplifier configured as an integrator. The output pulse of the first monostable multivibrator 26 is compared to a reference signal determined by a potentiometer. The integrator output is the error signal that exists between the reference signal, which represents the desired speed of the sinusoidal magnetic wave, and the precession pulse of the hall effect switch 24, which represents the actual speed of the sinusoidal magnetic wave.

This error signal is used to control the pulse width of a second monostable multivibrator 27. This second monostable multivibrator 27 is essentially a pulse width modulator that is triggered to generate an output pulse at a rate of 4.55 kHz; the pulse width of the output pulse is a function of the error signal. The second monostable multivibrator 27 or pulse width modulator drives the motor 20 through a MOSFET 28. The pulse width, which increases with the degree of error that exists between the actual speed and reference or desired speed of the sinusoidal magnetic wave, causes the motor 20 to turn the shaft faster, bringing the speed of the motor 20 to the desired speed.

Figure 6A:
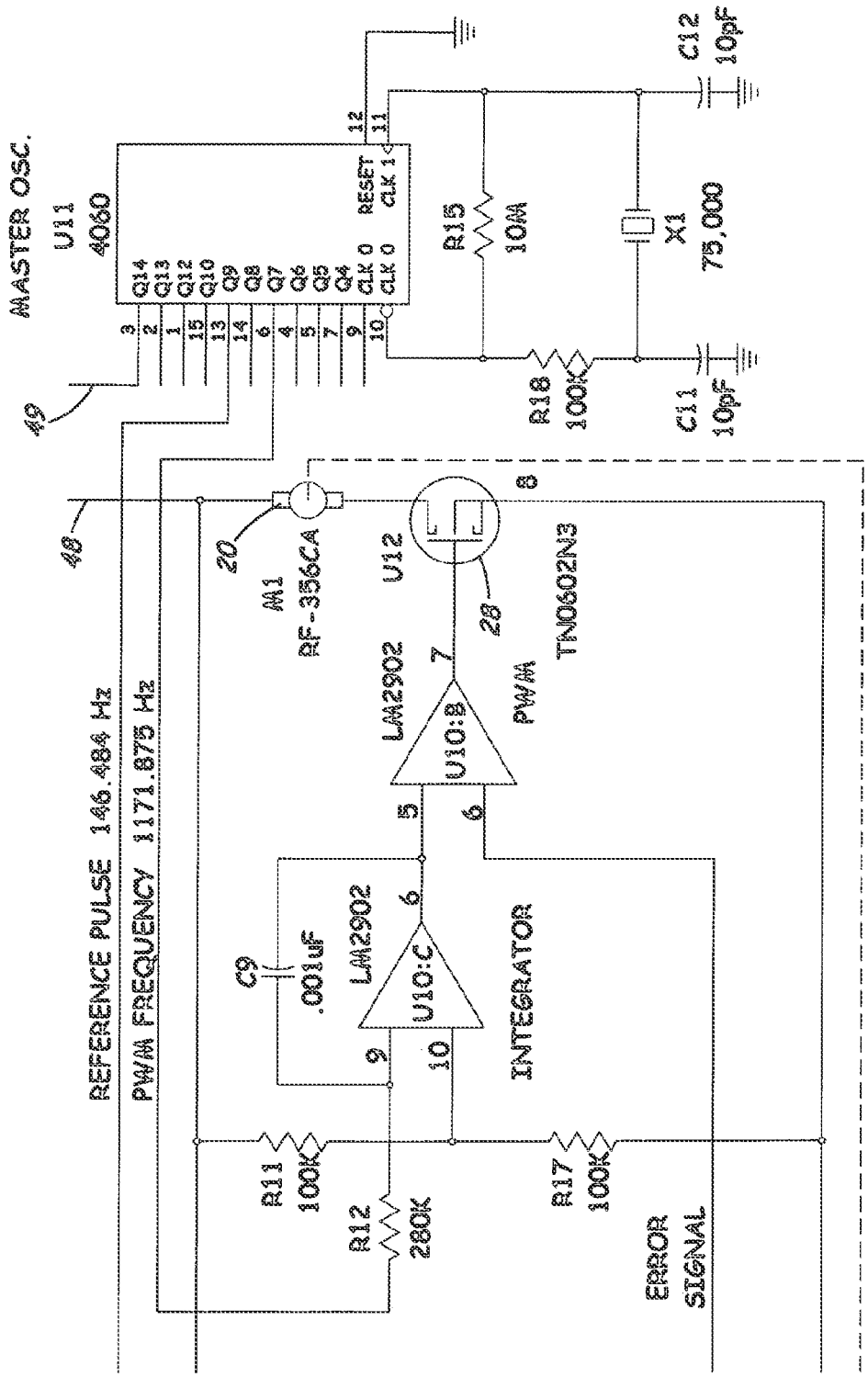
FIGS. 6A and 6B are circuit diagrams showing an alternative embodiment of the magnetic field generator.
Figure 6B:
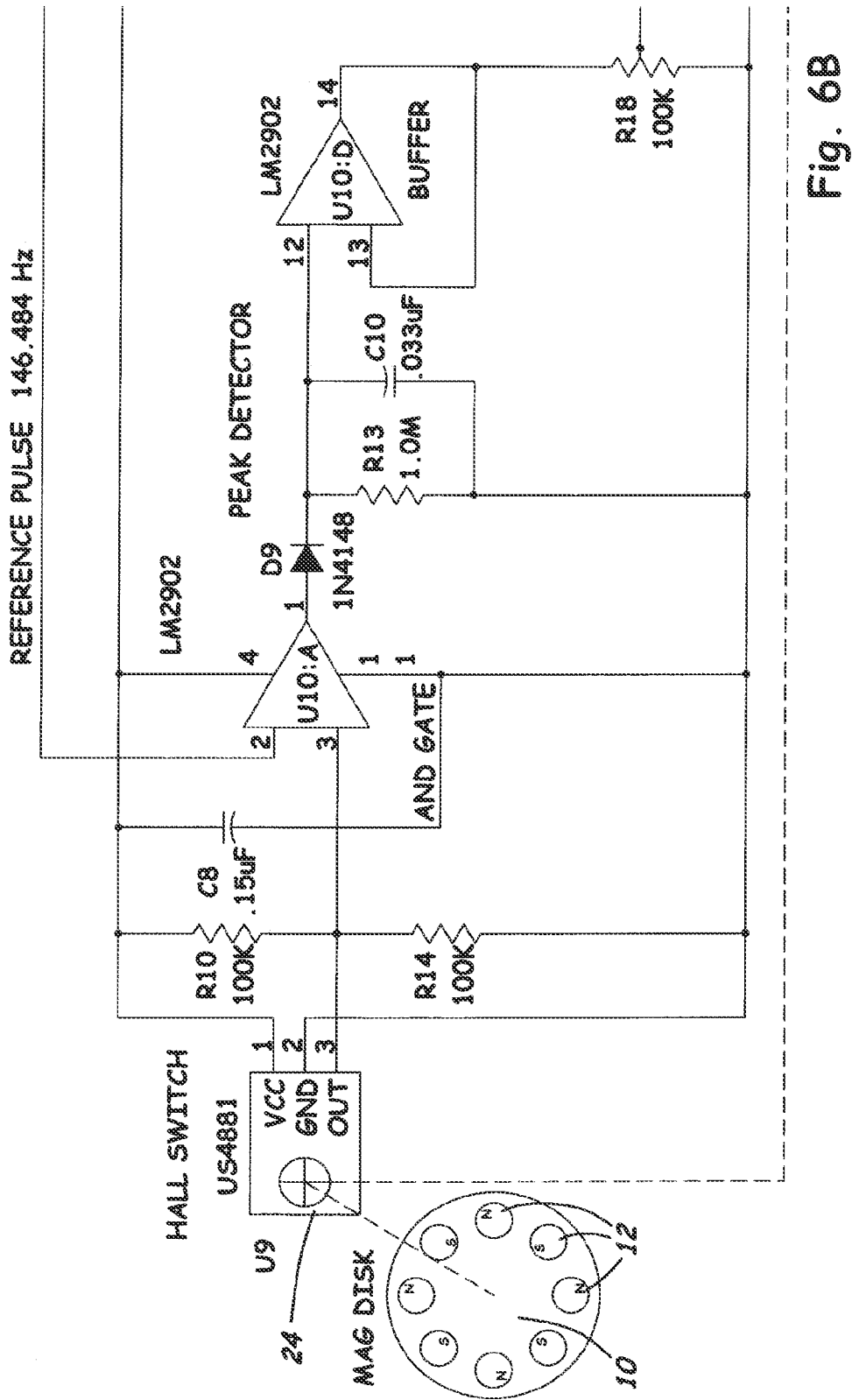

An alternative embodiment for the circuitry of the magnetic frequency generator is shown in FIGS. 6A and 6B.

In an embodiment using a stepper type motor 20, the controls needed to maintain a constant speed of rotation for the disk 10 would be considerably simpler. The controls would require a stepper motor driver integrated circuit; the speed would be controlled by the input frequency of the motor driver. There would be no need for a feedback path. However, stepper type motors are currently more expensive than brush type motors.

Figure 7B:
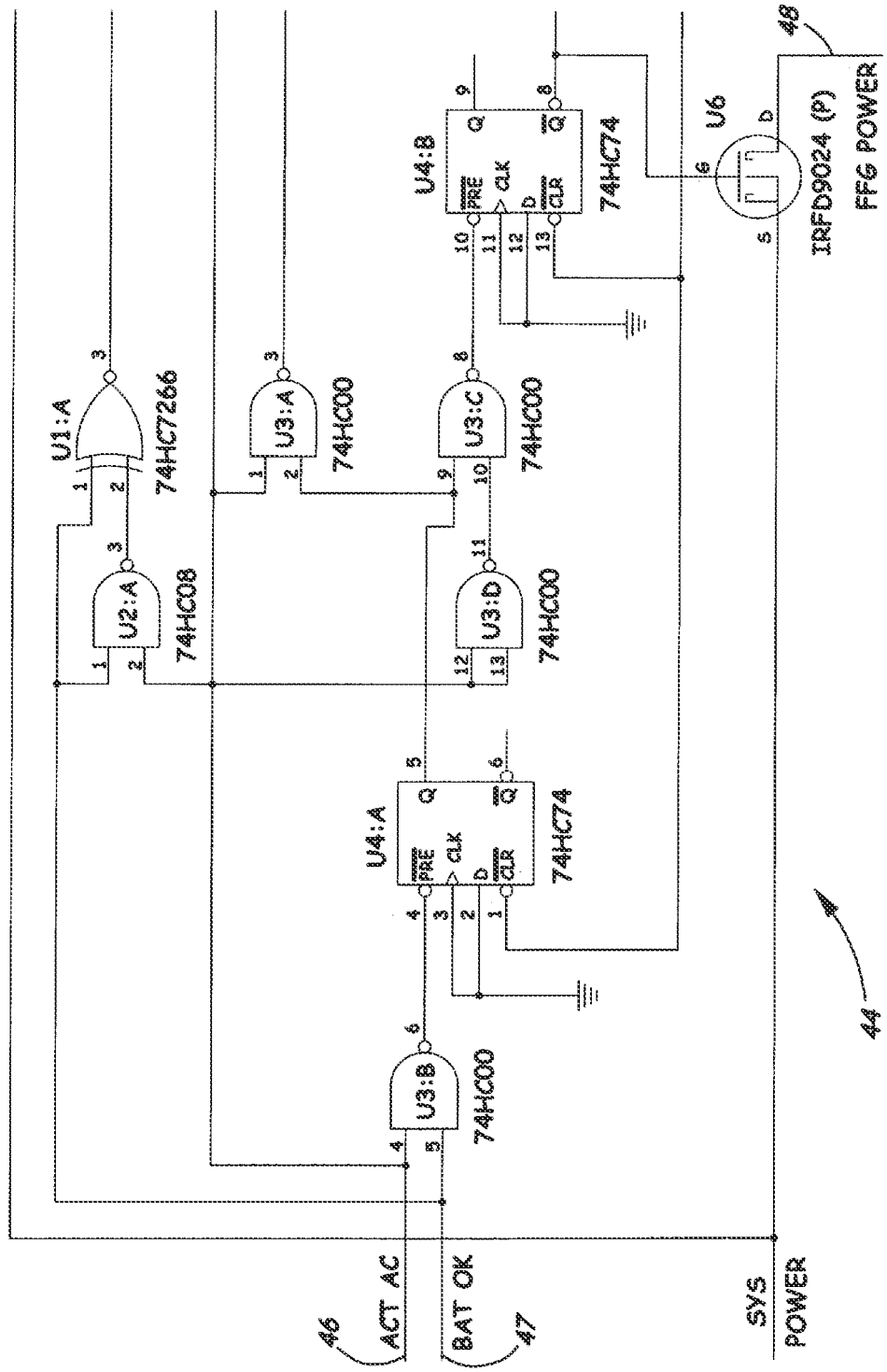
Figure 8:
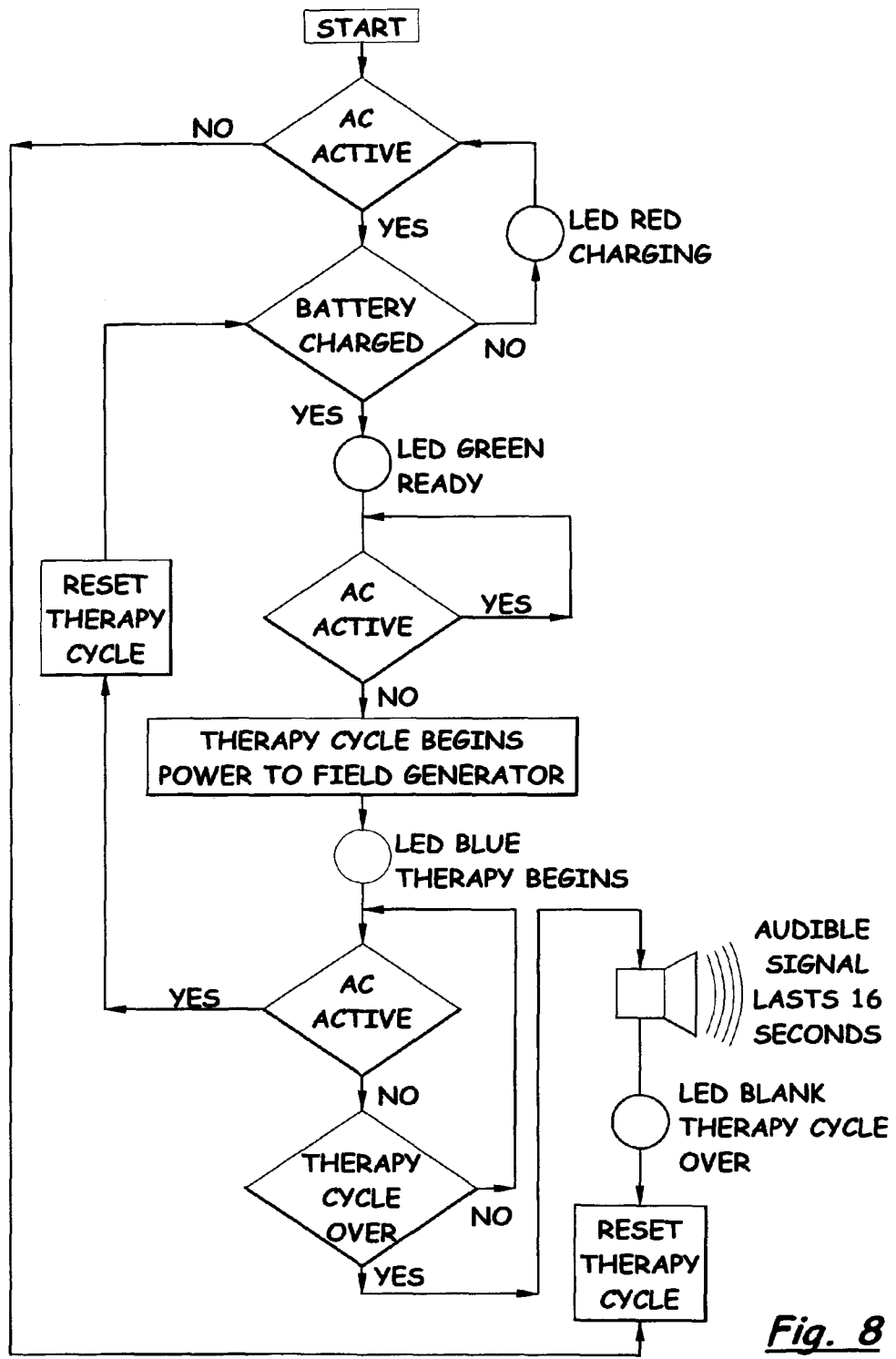
FIG. 8 is a flow chart showing the logical steps taken by the sequential controller in the preferred embodiment.

The sequential controller circuit 44, shown in FIGS. 7A and 7B, controls the therapy cycle. The sequential controller circuit 44 receives two signals from the battery charging circuit 34: (1) AC active 46, which is high when the ferrite rod 52 of the inductive probe 50 is in place and generating a high frequency magnetic field inside the probe insertion hole 30, and low when no such high frequency magnetic field is present inside the probe insertion hole 30; and (2) battery charged 47, which is high when the battery 36 is sufficiently charged to enable it to power one full therapy cycle, and low when the battery 36 is not sufficiently charged. The sequential controller circuit 44 uses high speed 74HC family CMOS integrated circuits to implement the design. The timing events take place with great accuracy due to the crystal time base X1. In the embodiment shown, the crystal time base X1 has a frequency of 75 kHz and a tolerance of ∓0.005%.

The sequential controller circuit 44 enables the inductive charging probe 50 to be used to start the therapy cycle. If the magnetic therapy device is inactive and the AC active signal 46 is low, meaning that there is no magnetic field present in the probe insertion hole 30 and receiver coil 32, then the magnetic therapy device will remain inactive. If the battery charged signal 47 is high, meaning that the battery has sufficient charge to power at least one therapy cycle, and the AC active signal 46 is high, meaning that there is a magnetic field present in the probe insertion hole 30 and receiver coil 32, then the sequential controller circuit 44 will wait for the AC active signal 46 to become low, at which point it will begin the therapy cycle by causing the motor 20 to spin the disk 10 for thirty minutes. With sixteen seconds left in the therapy cycle, a speaker 43 will emit an audible signal, informing the user that the therapy cycle is almost over. After thirty minutes, the sequential controller circuit 44 will cause the motor 20 to stop spinning the disk 10, ending the therapy cycle.

In one embodiment, the tri-state LED 42 has three colors, namely red, green, and blue, which indicate the status of the battery 20 and the therapy cycle. The tri-state LED 42 emits red when the motor 20 is not causing the disk 10 to spin, the AC active signal 46 is high, meaning that the battery 36 is charging, and the battery charged signal 47 is low, meaning that the battery 36 does not have sufficient charge to power a full therapy cycle. The tri-state LED 42 emits green when the motor 20 is not causing the disk 10 to spin, the AC active signal 46 is high, meaning that the battery 36 is charging, and the battery charged signal 47 is high, meaning that the battery 36 does have sufficient charge to power a full therapy cycle. The tri-state LED 42 emits blue when the therapy cycle is in effect and the motor 20 is causing the disk 10 to spin. When the therapy cycle is not in effect, meaning that the motor 20 is not causing the disk 10 to spin, and the AC active signal 46 is low, the tri-state LED 42 is blank, not emitting any color.

Figure 9:
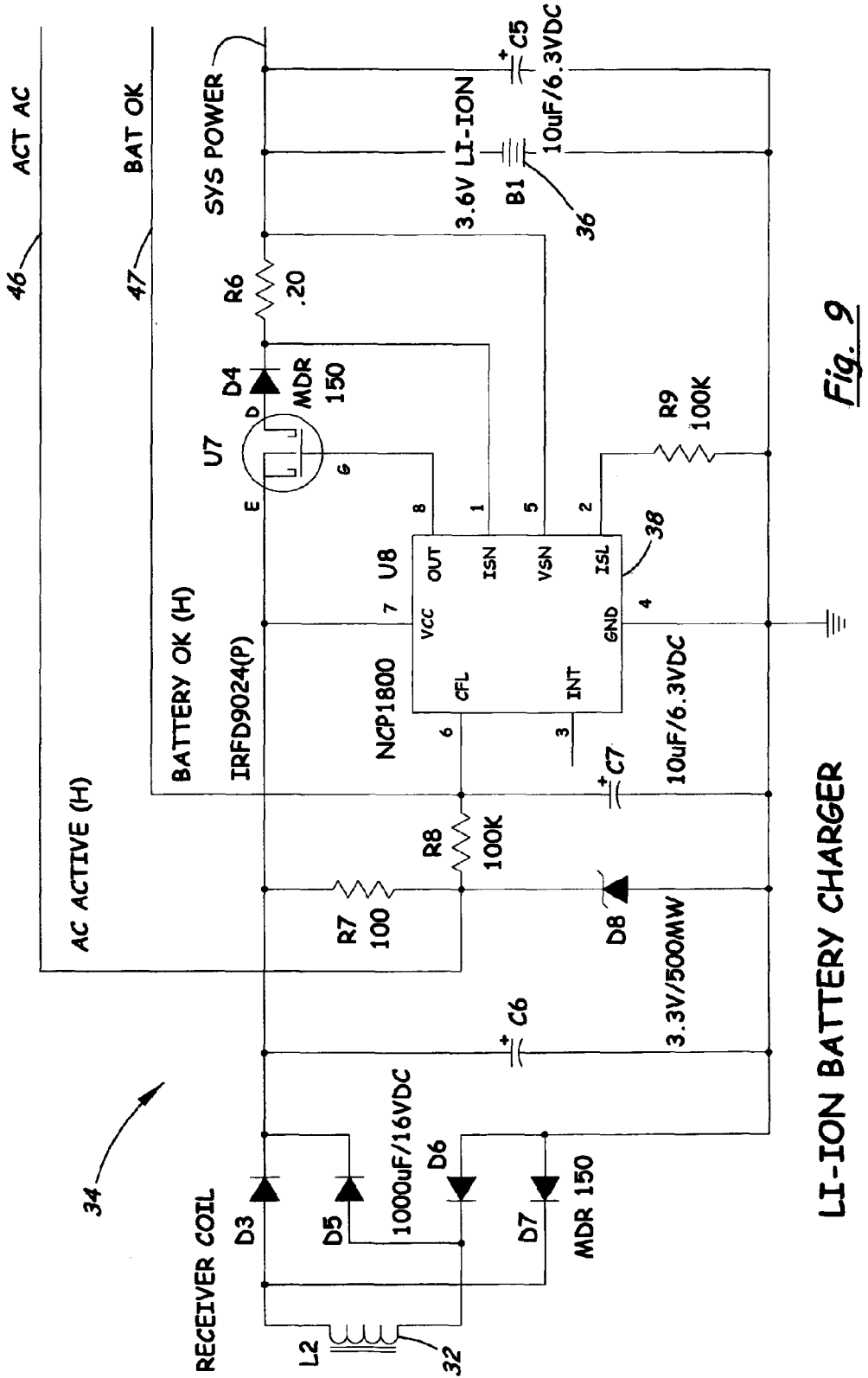
FIG. 9 is a circuit diagram showing the preferred embodiment of the battery charging circuit.

FIG. 9 is a flowchart showing the above-described pattern of events. When the therapy cycle is over or not in effect, the tri-state LED 42 is blank. When the inductive charging probe 50 is inserted into the probe insertion hole 30, causing the AC active signal 46 to become high, the sequential controller circuit 44 checks the battery charged signal 47. If the battery charged signal 47 is low, then the tri-state LED 42 will emit red until one of two events happens: (1) the AC active signal 46 becomes low, at which point the therapy cycle will be reset and the tri-state LED 42 will go blank; or (2) the battery charged signal 47 becomes high, at which point the tri-state LED 42 will emit green. With the battery charged signal 47 high and the AC active signal 46 high, the battery 36 is charging (unless it is fully charged), and the tri-state LED 42 emits green until the AC active signal 46 becomes low. When the AC active signal 46 becomes low, the therapy cycle begins, and the tri-state LED 42 emits a flashing blue signal while the therapy cycle is in effect. Sixteen seconds before the therapy cycle has run its thirty-minute course, the speaker 43 emits an audible signal, and at the end of the thirty minutes, the therapy cycle ends, the motor 20 stops causing the disk 10 to spin, and the tri-state LED becomes blank. The therapy cycle can be restarted by inserting and removing the inductive charging probe 50 from the probe insertion hole 30.

It is envisioned that different time durations than thirty minutes could be used for the therapy cycle. Also, design alternatives to the shown circuitry include a microcontroller operating under software control or a microprocessor, either of which could utilize an infrared data link to enable non-contact programming of the magnetic field frequency, duration of therapy, and individual program profiles. Or, a programmable logic array could be used. These design alternatives would be advantageous for large scale production. It is also envisioned that instead of using the inductive charging probe 50 to control the therapy cycle, a button could be installed onto the housing 5 and connected to the sequential controller circuit 44 to control the therapy cycle; the button should be designed to prevent any water or other liquid from entering the device from outside the housing.

In one embodiment of the power supply, the battery 36 is rechargeable and non-magnetic. The battery 36 is rechargeable so that the device can be reused without having to disassemble the device and replace the battery 36, allowing the device to be completely sealed and waterproof. The battery 36 is non-magnetic so that it will not create a magnetic drag on the disk 10. In one embodiment, the battery 36 is a 3.7 volt, 1500 milliampere-hour, Prismatic Lithium-Ion battery. This terminal voltage of 3.7 volts is high enough to operate the electronic components of the magnetic therapy device without using a step-up DC to DC converter. This Prismatic Lithium-Ion battery, which is a Prismatic Polymer type, is non-magnetic, and has the highest energy density of all available rechargeable batteries, allowing the device to be small and efficient. The Prismatic Lithium-Ion battery can be recharged many times, and can operate the magnetic therapy device for at least twenty continuous hours before recharging, allowing for forty back-to-back thirty-minute therapy cycles before the device needs to be recharged for two hours.

Figure 10:
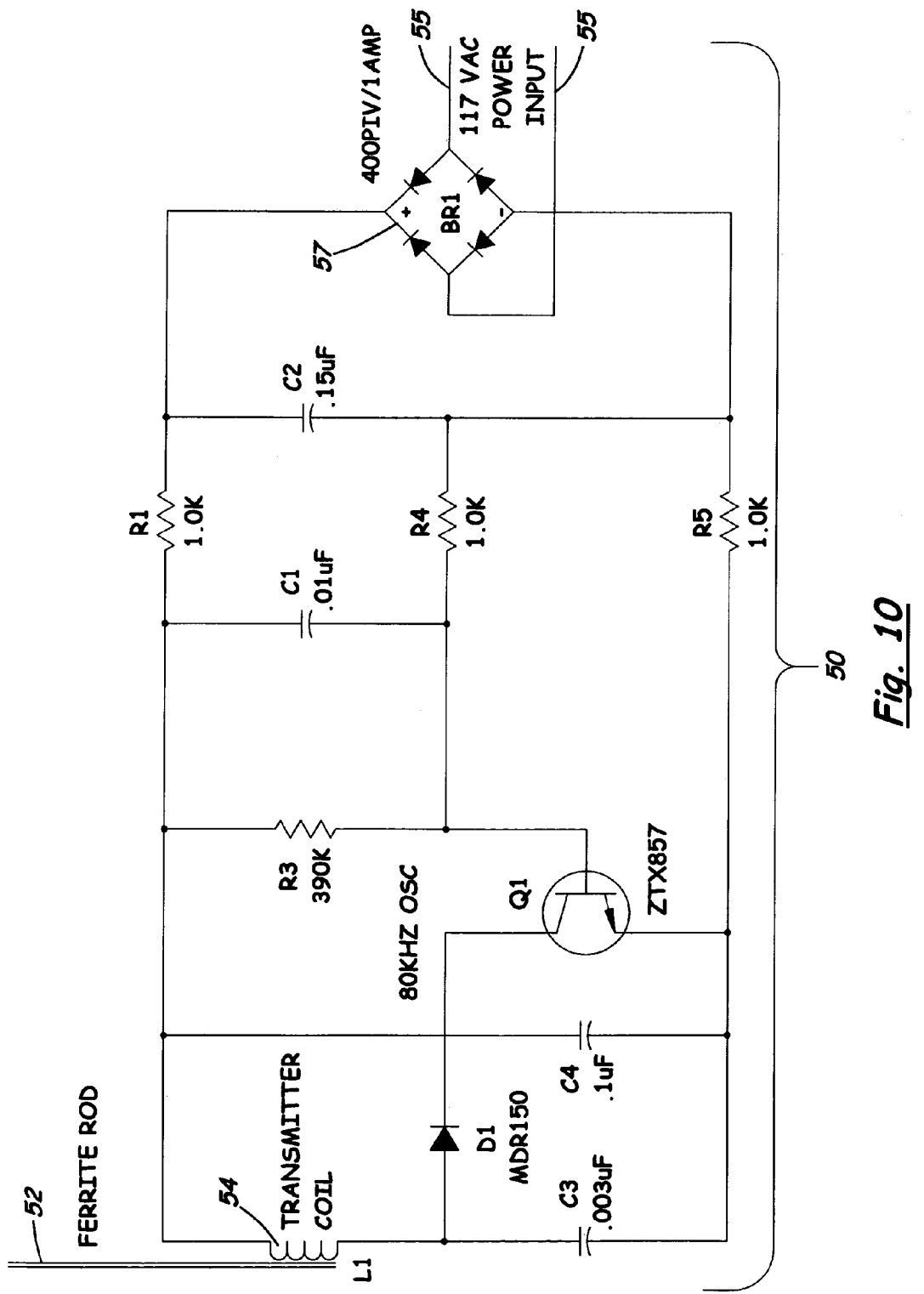
FIG. 10 is a circuit diagram showing the preferred embodiment of the circuitry for the inductive probe that generates the magnetic field used to charge the battery.

The battery charging circuit 34, shown in FIG. 10, receives power from an inductive coil, the receiver coil 32. The receiver coil 32 receives power from a high frequency magnetic field created by the transmitter coil 54 of the battery charging circuit 50. The receiver coil 32 is inductively coupled to the transmitter coil 54 by a ferrite rod 52 when the inductive charging probe 52 is inserted into the probe insertion hole 30. The receiver coil 32 surrounds the probe insertion hole 30; the probe insertion hole 30 is a recessed portion of the housing 30 and is made from the same material as the housing 5. The magnetic field created by the transmitter coil 54 and ferrite rod 52 induces a high-frequency AC current in the receiver coil 32. This high-frequency current output from the receiver coil 32 is rectified using high speed diodes in a bridge configuration (D3, D5, D6, D7). This rectified current is converted to DC using an electrolytic filtering capacitor (C6).

Recharging Lithium-Ion batteries requires a special charging sequence of current and voltage. In one embodiment, this charging sequence is handled in the battery charging circuit 34 by a Motorola NCP1800 integrated circuit 38. The battery charging circuit 34 shares two control signals with the sequential controller circuit 44: AC active 46, and battery charged 47. These control signals 46, 47, in combination with the battery charging circuit 50, enable the battery 36 to be fully recharged by the magnetic field generated by the transmitter coil 54 and ferrite rod 52. The combined circuitry of the sequential controller circuit 44 and the battery charging circuit 34 causes the therapy cycle to begin when the inductive charging probe 52 is removed from the probe insertion hole 30 if the battery 36 was sufficiently charged to power one full therapy cycle.

The circuitry for one embodiment of the inductive charging probe 50 is shown in FIG. 10. The inductive charging probe 50 generates a well focused magnetic field to power the receiver coil 32 and the battery 36. The inductive charging probe 50 also serves as operator control of the magnetic therapy device by controlling the voltage of the receiver coil 32. The use of the inductive charging probe 50 as operator control obviates the need for switches or moving parts outside the housing 5. When the inductive charging probe 50 is removed from the probe insertion hole 30, the receiver coil 32 voltage drops to zero, and if the battery 36 was sufficiently charged to power one full therapy cycle, then the therapy cycle will begin. This enables the battery 36 to be charged and the magnetic therapy device to be controlled in a completely sealed housing 5 without any electrical contacts outside the housing 5. Thus, the magnetic therapy device will still operate even if it completely submerged in water and used in a bathtub without risk of electric shock.

The ferrite rod 52 is part of the inductive charging probe 50 and is inductively coupled to the transmit coil 54. The transmit coil 54 is operated at high frequency, typically 85 kHz. This frequency is needed to increase the efficiency of the coupling between the transmitter coil 54 and the receiver coil 32 because the magnetic geometry between these two elements is not ideal, resulting in a loss of power.

The power input 55 of the inductive charging probe 50 receives 117 Volts AC from a wall outlet. This AC input is rectified with a bridge rectifier 57, and this rectified wave is converted to high voltage DC by a second electrolytic capacitor C2. A high voltage NPN transistor Q1 configured as an RC oscillator is operated by DC voltage from a first electrolytic capacitor C2 and drives the transmitter coil 54 at 85 kHz.

Figure 11:
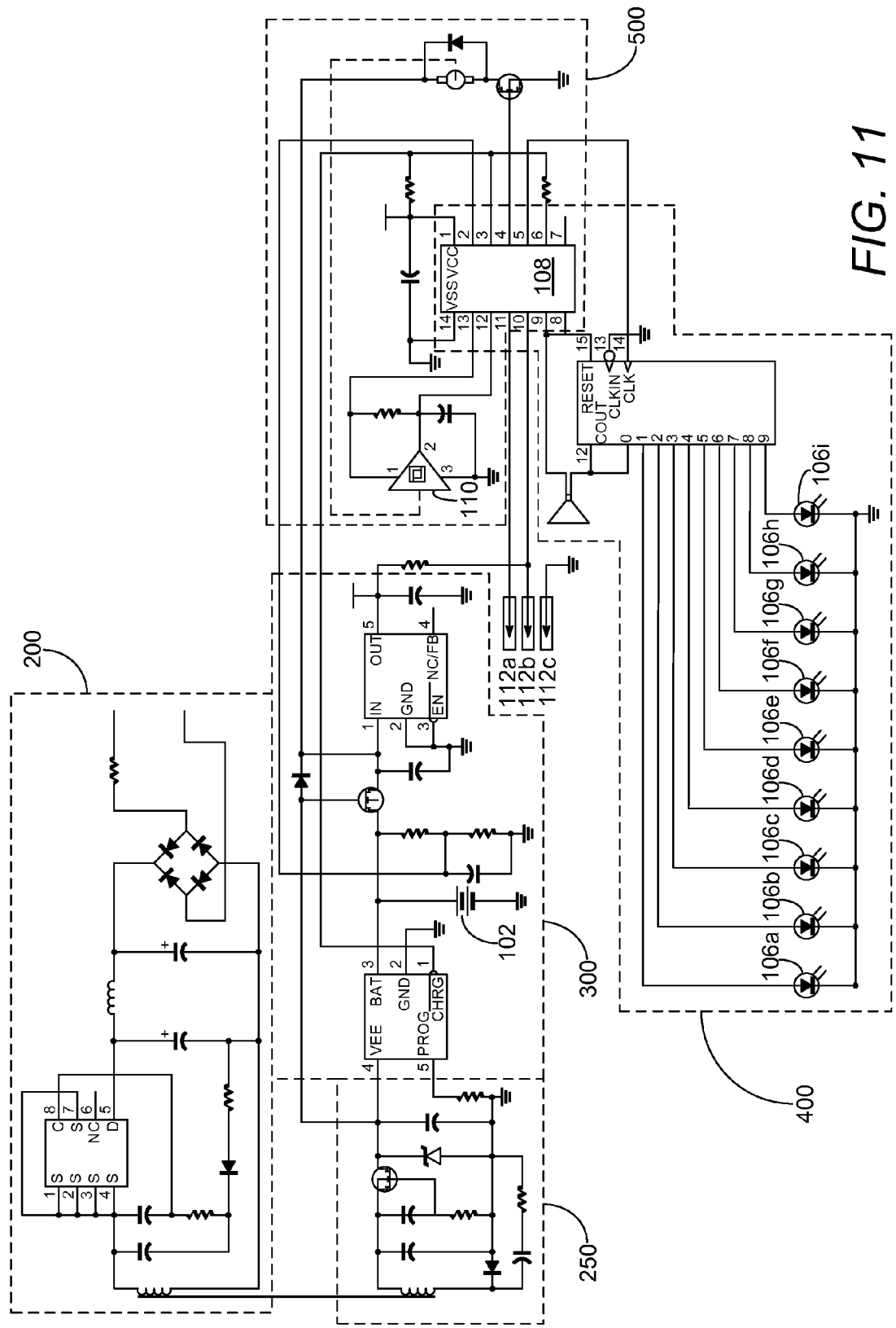
FIG. 11 is a circuit diagram showing a system according to an example embodiment.

FIG. 11 is a circuit diagram showing a system 100 according to an example embodiment. According to this example, the system 100 may include a charging probe circuit 200. The charging probe circuit 200 may, for example, receive current from an alternating current source an induce a magnetic field. The charging probe circuit 200 is described further with reference to FIG. 12.

The system 100 may also include a current inducing circuit 250. The current inducing circuit 250 may carry a current induced by a magnetic field such as the magnetic field induced by the charging probe circuit 200. The current inducing circuit 250 may produce an electrical output based on the magnetic field. The current inducing circuit 250 is described in further detail with reference to FIG. 12.

The system 100 may also include a battery charging circuit 300. The battery charging circuit 300 may receive a voltage source, such as the electrical output of the current inducing circuit, and recharge a rechargeable battery 102 with the voltage source. The battery charging circuit 300 may supply power to a motor 104. The battery charging circuit 300 may, for example, allow current to flow from the voltage source to the motor 104. The battery charging circuit 300 may also enable the rechargeable battery 102 to supply power to the motor 104 when a voltage of the voltage source drops below a threshold voltage level, according to an example embodiment. The battery charging circuit 300 is described in further detail with reference to FIG. 13.

The system 100 may also include a visual indicating circuit 400. The visual indicating circuit 400 may, for example, include a plurality of visual indicators 106a, 106b, 106c, 106d, 106e, 106f, 106g, 106h, 106i and a microprocessor 108 which monitors a voltage level of a rechargeable battery, such as the rechargeable battery 102 included in the battery charging circuit 300. The visual indicating circuit 400 may light a number of the plurality of visual indicators 106a, 106b, 106c, 106d, 106e, 106f, 106g, 106h, 106i based on a monitored voltage level of the rechargeable battery 102, according to an example embodiment. The visual indicating circuit 400 is described in further detail with reference to FIG. 14.

Figure 15A:
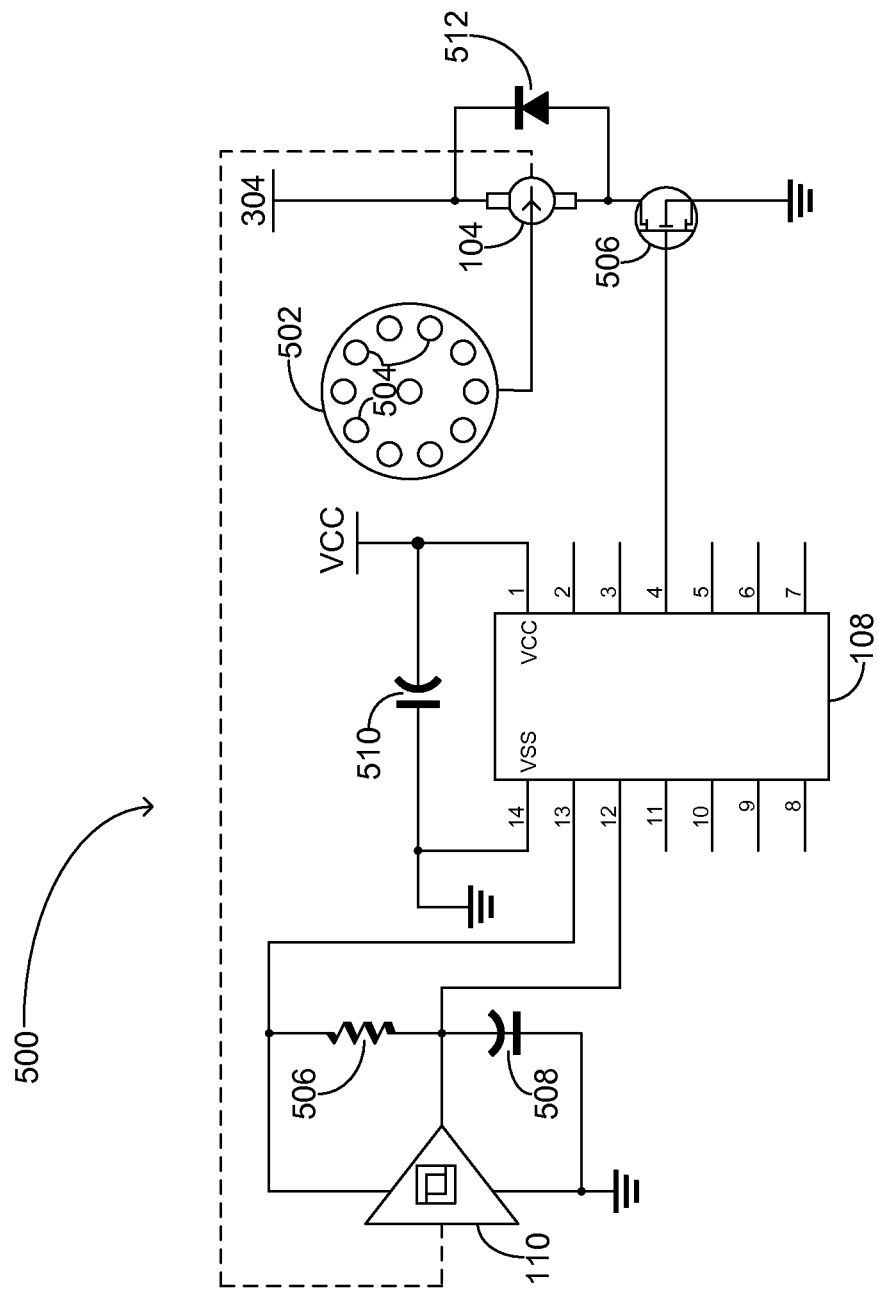
FIG. 15A is a circuit diagram showing a tachometer circuit according to an example embodiment.

The system 100 may also include a tachometer circuit 500. The tachometer circuit 500 may include a motor 104 which controls a disk (shown in FIG. 16D) upon which is mounted a plurality of magnets (also shown in FIG. 16D). The tachometer circuit 500 may also include a tachometer 110 which monitors a magnetic field generated by the plurality of magnets and provides a signal to a microprocessor based on the monitored magnetic field. The tachometer circuit 500 may also include a microprocessor, which may be the same microprocessor 108 used by the visual indicating circuit 400, which controls the motor 104 based on the signal received from the tachometer 110. The tachometer circuit 500 is described further with reference to FIG. 15.

The system 100 may include one or more microprocessor inputs 112a, 112b, and may include an input ground 112c. The microprocessor inputs 112a, 112b may be used to program the microprocessor 108, such as by use of a personal computer (not shown), according to an example embodiment.

Figure 12:
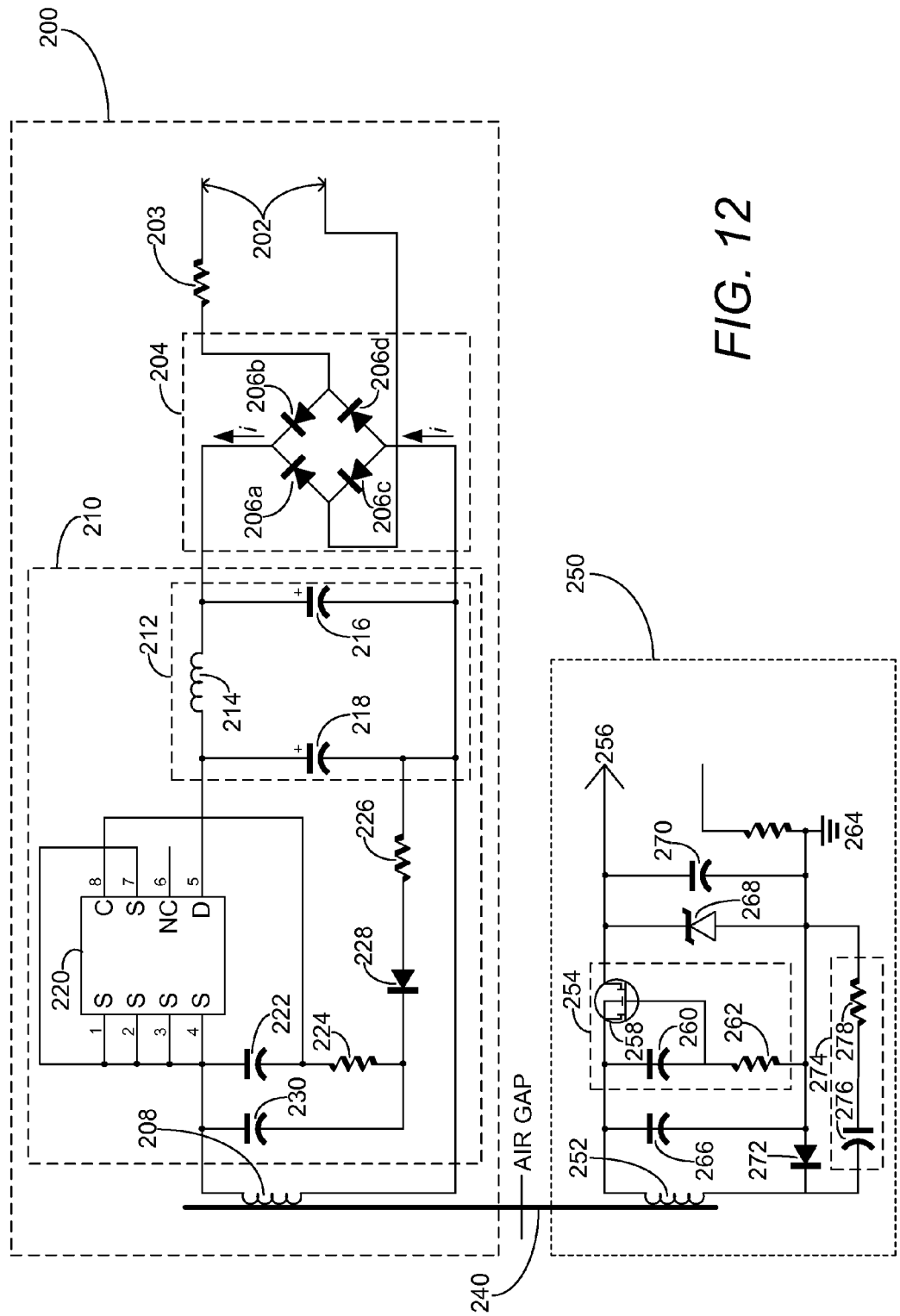
FIG. 12 is a circuit diagram showing a charging probe circuit and current inducing circuit according to an example embodiment.

FIG. 12 is a circuit diagram showing the charging probe circuit 200 and current inducing circuit 250 according to an example embodiment. According to this example, the charging probe circuit 200 may include an alternating current (AC) input 202. The AC input 202 may receive current from an AC source (not shown), such as an electrical wall outlet (not shown). The AC input 202 may, for example, receive inputs between approximately 85 to 264 volts AC between approximately 47 and 64 Hertz. This may allow the charging probe circuit 200 to receive input from many electrical wall outlets.

The AC input 202 may be coupled to a rectifier circuit 204. The rectifier circuit 204 may rectify the current received by the AC input 202 from the AC source. The rectifier circuit 204 may include a bridge rectifier circuit. The rectifier circuit 204 may, for example, include a plurality, such as four, diodes 206a, 206b, 206c, 206d which allow current to flow through the rectifier circuit 204 in only one direction, such as the direction denoted i in FIG. 12.

One of the AC input 202 nodes may be coupled to the rectifier circuit 204 via a resistor 203. The resistor 203 may, for example, include a flameproof fusible resistor. The resistor 203 may protect against fault conditions. In an example embodiment, The charging probe circuit may also include a primary coil 208 and a control circuit 210. The control circuit 210 may convert the rectified current into a regulated voltage across the primary coil 208. The primary coil 208 may induce a magnetic field from the regulated voltage. The magnetic field may, for example, have a frequency between about ten Hertz and about one hundred Hertz.

The primary coil 208 may include a first end coupled to the control circuit 210 and a second end coupled to the rectifier circuit 204. The primary coil 208 may, in an example embodiment, extend away from the AC input 202, rectifier circuit 204, and control circuit 210. The primary coil 208 may be enclosed in a probe, as described further with reference to FIG. 16B.

In an example embodiment, the control circuit 210 may include a Pi filter 212. The Pi filter 212 may reduce ripple voltage across the rectifier circuit 204. The Pi filter 212 may, for example, include an inductor 214, a first capacitor 216, and a second capacitor 218. The input capacitance may be split between the first capacitor 216 and the second capacitor 218 to allow the Pi filter 212 to be formed by the inductor 214. The Pi filter 212. The Pi filter 212 may, for example, filter noise associated with the AC source.

The first capacitor 216 and second capacitor 218 may have capacitance values of, for example, approximately 4.7 microfarads and approximately 400 volts. The inductor 214 may, for example, have an inductance of approximately one milli-Henry. The first capacitor 216 may have a first end coupled to a first end of the rectifier circuit 204 and to a first end of the inductor 214, and a second end coupled to a second end of the rectifier circuit 204 and to a first end of the primary coil 208. The first end of the inductor 214 may be coupled to the first end of the first capacitor 216 and to the first end of the rectifier circuit 204; a second end of the inductor 214 may be coupled to a first end of the second capacitor 218. A first end of the second capacitor 218 may be coupled to the second end of the inductor 214, and a second end of the second capacitor 218 may be coupled to the second end of the rectifier circuit 204 and the first end of the primary coil 208.

The control circuit 210 may also include an off-line regulator 220. The off-line regulator 220 may, for example, include a Power Integrations LK500, an integrated circuit which combines a 700 volt high voltage metal-oxide-semiconductor field-effect transistor (MOSFET), pulse-width modulation controller, startup, thermal shutdown, and fault protection circuitry.

The off-line regulator 220 may regulate the voltage across the primary coil 208. The off-line regulator 220 may, for example, be coupled to the primary coil 208. In an example embodiment, the off-line regulator 220 may be coupled to the second end of the inductor 214, and the rectifier circuit 204 may be coupled to the first end of the inductor 214.

In an example embodiment, the control circuit 210 may include a third capacitor 222 coupled to the primary coil 208. In this example, the off-line regulator 220 may regulate the voltage across the primary coil 208 by controlling a voltage across the third capacitor 222. The off-line regulator 220 may control the voltage across the third capacitor 222 by controlling a current flowing into or out of the off-line regulator 220 based on the voltage across the third capacitor 222. The third capacitor 222 may, for example, have a capacitance of 0.22 microfarads and approximately 50 volts.

For example, when power is applied, a high DC voltage may appear at a drain D of the off-line regulator 220. The third capacitor 222 may be charged through a switched high voltage current source connected internally between the drain D and a control C of the of the off-line regulator 220. When a voltage at the control C reaches approximately 5.7 volts relative to a source S of the off-line regulator 220, the internal current source of the off-line regulator 220 may be turned off. The internal control circuitry of the off-line regulator 220 may be activated and the high voltage internal MOSFET of the off-line regulator 220 may start to switch, using the energy stored in the third capacitor 222 to power the off-line regulator 220. As current ramps up in the primary coil 208, energy may be stored in the primary coil 208. The energy stored in the primary coil 208 may be delivered to the current inducing circuit 250 each cycle when the MOSFET turns off.

In another example, the off-line regulator 220 may include a source S coupled to a first end of the primary coil 208 and the drain D coupled to a first end of the second capacitor 218. In this example, the first end of the second capacitor 218 may be coupled to the drain D of the off-line regulator 220 and the second end coupled to the second end of the primary coil 208.

In an example embodiment, the drain D of the off-line regulator 220 may also be coupled to the second end of the inductor 214. A control C of the off-line regulator 220 may be coupled to a first end of the third capacitor 222. The source S of the off-line regulator 220 may also be coupled to a second end of the third capacitor 222 and to the first end of the primary coil 208.

In another example, the control circuit 210 may also include a first resistor 224, a second resistor 226, a diode 228, and a fourth capacitor 230. The diode 228 and fourth capacitor 230 may form a clamp network maintaining a voltage $V_{OR}$ at the first end of the primary coil 208. The diode 228 may include a fast ($t_{rr}$<250 nanoseconds) or ultra-fast diode to prevent the voltage across the off-line regulator 220 from reversing and ringing below ground. The second resistor 226 may filter leakage inductance.

The first resistor 224 may, for example, have a resistance of about 59.3 kiloohms. The fourth capacitor 230 may, for example, have a capacitance of one microfarad and 100 volts.

In an example embodiment, the fourth capacitor 230 may include a first end coupled to the source S of the off-line regulator 220 and to the first end of the primary coil 208. The fourth capacitor 230 may also include a second end coupled to a first end of the first resistor 224 and to a cathode end of the diode 228. The first resistor 224 may include a first end coupled to the second end of the fourth capacitor 230 and to the cathode end of the diode 228. A second end of the first resistor 224 may also include a second end coupled to the first end of the third capacitor 222 and to the control C. The diode 228 may include the cathode end coupled to the first end of the first resistor 224 and to the second end of the fourth capacitor 230, and an anode end coupled to a first end of the second resistor 226. The second resistor 226 may include the first end coupled to the anode end of the diode 228, and a second end coupled to the second end of the second capacitor 218, the second end of the first capacitor 216, the bridge circuit 204, and the second end of the primary coil 208.

The off-line regulator 220 may, for example, include three operating modes. In a startup mode, an output voltage across the fourth capacitor 230 may increase, and a current through the first resistor 224 and into the control C may increase from approximately zero to two milliamperes. In a regulate mode, the off-line regulator 220 may maintain a constant voltage across the third capacitor 222 by turning current into the control C off when the voltage across the third capacitor 222 increases, and turn the current into the control C on when the voltage across the third capacitor 222 decreases. In an auto-restart mode, which may be triggered by the voltage across the third capacitor falling so that the current into the control C falls below approximately one milliampere, the off-line regulator 220 may return to the startup mode. The third capacitor 222 may set the auto-restart period and the time for reaching the regulate mode before entering the auto-restart mode from the start-up mode.

The current inducing circuit 250 may include a secondary coil 252. The secondary coil 252 may carry a current induced by a changing magnetic field, such as the magnetic field induced by the primary coil 208. The solid line 240 indicates the magnetic coupling between the primary coil 208 and the secondary coil 252. The secondary coil 252 may, for example, include a wire such as a copper wire wrapped around a pot core. The secondary coil 252 may surround an aperture (not shown in FIG. 12) which receives the probe which surrounds the primary coil 208, with, for example, an air gap, such as an air gap of about 0.001 inches; the aperture is described further with reference to FIG. 16A.

The primary coil 208 and secondary coil 252 may form an isolation transformer with the coils of the primary coil 208 and secondary coil 252 wound around individual bobbins separated by the air gap. The transformer may be constructed in two sections corresponding to the primary coil 208 and the secondary coil 252, each wound on separate bobbins using one half of the pot core and separated by the magnetic air gap of 0.001 inches. The transformer may be designed to be discontinuous, so that energy may be transferred during the off time of the transistor 258.

The current inducing circuit 250 may include a delay switch 254 coupled to the secondary coil 252 and an output node 256 coupled to the delay switch 254. The delay switch 254 may delay the current carried by the secondary coil 252 from reaching the output node 256 to allow an output voltage of the output node 256 to reach a regulation voltage. The output node 256 may, for example, provide a voltage of approximately five volts direct current (DC) and 400 milliamperes.

The delay switch 254 may, for example, include a transistor 258, a first capacitor 260, and a first resistor 262. The transistor 258 may include a first end and a second end of a channel (such as a source and a drain) and a control node (such as a gate) which controls a resistance across the channel. The first end may be coupled to a first end of the secondary coil 252 and to a first end of the first capacitor 260. The second end may be coupled to the output node 256. The control node may be coupled to a second end of the first capacitor 260, all according to an example embodiment.

The first end of the first capacitor 260 may be coupled to the first end of the secondary coil 252 and to the first end of the channel of the transistor 258. The second end of the first capacitor 260 may be coupled to the control node of the transistor 258. A first end of the first resistor 262 may include a first end coupled to the second end of the first capacitor 260 and to the control node of the transistor 258, and a second end coupled to ground 264, all according to an example embodiment.

In an example embodiment, the transistor 258 may include a metal-oxide-semiconductor field-effect transistor (MOSFET). The transistor 258 may, for example, include a p-channel MOSFET. The channel may include a source-drain channel of the MOSFET, and the first end and second end may include a source and a drain, or vice versa. Also in this example, the control node may include a gate of the MOSFET.

The delay cause by the delay switch 254 may be a function of the RC time constant of the first capacitor 260 and the first resistor 262 and the saturation threshold of the transistor 258. In an example in which the first capacitor 260 has a capacitance of approximately 0.15 microfarads and the first resistor 262 has a resistance of approximately one megaohm, the delay may be 150 milleseconds.

In an example embodiment, the current inducing circuit 250 may include a second capacitor 266. The second capacitor 266 may rectify and filter the output of the secondary coil 252 to provide a DC output at the output node 256.

The second capacitor 266 may have a capacitance of, for example, 22 microfarads and 63 volts. A first end of the second capacitor 266 may be coupled to the first end of the secondary coil 252, the first end of the first capacitor 260, and to the first end of the channel of the transistor 258. A second end of the second capacitor 266 may be coupled to the second end of the first resistor 262 and to ground 264, all according to an example embodiment.

Also in an example embodiment, the current inducing circuit 250 may include a first diode 268 and a third capacitor 270. The first diode 268 may, for example, include a Zener diode. The first diode 268 may prevent a voltage of the output node 256 from exceeding a breakdown voltage of the first diode 268, such as approximately 5.6 volts. The third capacitor 270 may reduce ripples in the voltage of the output node 256.

The third capacitor 270 may, for example, have a capacitance of 1000 microfarads and 6.3 volts. The first diode 268 may include a cathode end coupled to the second end of the channel of the transistor 258, to the output 256, and to a first end of the third capacitor 270. The first diode 268 may also include an anode end coupled to a second end of the third capacitor 270, to the ground 264, to the second end of the first resistor 262, and to the second end of the second capacitor 266. The first end of the third capacitor 270 may be coupled to the second end of the channel of the transistor 258, to the first end of the first diode 268, and to the output node 256. The second end of the third capacitor 270 may be coupled to ground 264, to the second end of the first diode 268, to the second end of the first resistor 262, and to the second end of the second capacitor 266, all according to an example embodiment.

In an example embodiment, the current inducing circuit 250 may include a second diode 272, such as a Schottky diode. The second diode 272 may rectify the output of the secondary coil 252 to provide a DC output at the output 256. The second diode 272 may include a cathode end coupled to a second end of the secondary coil, and an anode end coupled to the second end of the second capacitor 266, to the second end of the first resistor 262, to the anode end of the first diode 268, to the second end of the second capacitor 266, and to ground 264.

In an example embodiment, the current inducing circuit 250 may include a snubber circuit 274. The snubber circuit 274 may reduce transient voltages between the second end of the secondary coil 252 and the ground 264. The snubber circuit 274 may also attenuate conducted electromagnetic interference, such as in high frequency bands.

The snubber circuit 274 may, for example, include a fourth capacitor 276 and a second resistor 278 connected in series. The fourth capacitor 276 may have a capacitance of 0.001 microfarads and 100 volts, according to an example embodiment. A first end of the snubber circuit 274 or series may be coupled to the second end of the secondary coil 252 and to the cathode end of the second diode 272. A second end of the snubber circuit 274 or series may be coupled to the anode end of the second diode 272, to the second end of the second capacitor 266, to the second end of the first resistor 262, to the anode end of the first diode 268, to the second end of the third capacitor 270, and to ground 264, all according to an example embodiment.

Figure 16A:
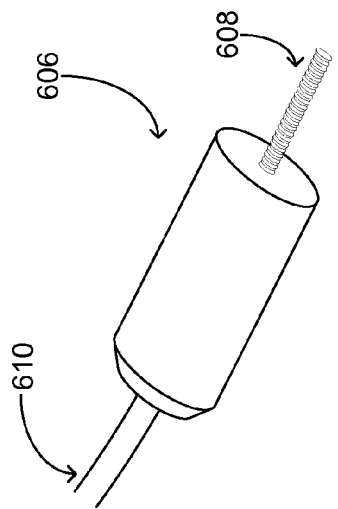
FIG. 16A is an illustration of a magnetic therapy device according to an example embodiment.

In an example embodiment, the current inducing circuit 250 may be included in a disk-shaped housing, such as the housing shown in FIG. 16A. The disk-shaped housing may enclose a disk with a plurality of magnets mounted onto the disk, such as the disk shown in FIG. 16D. The disk may rotate based on power received from the output node 256, according to an example embodiment.

Figure 13:
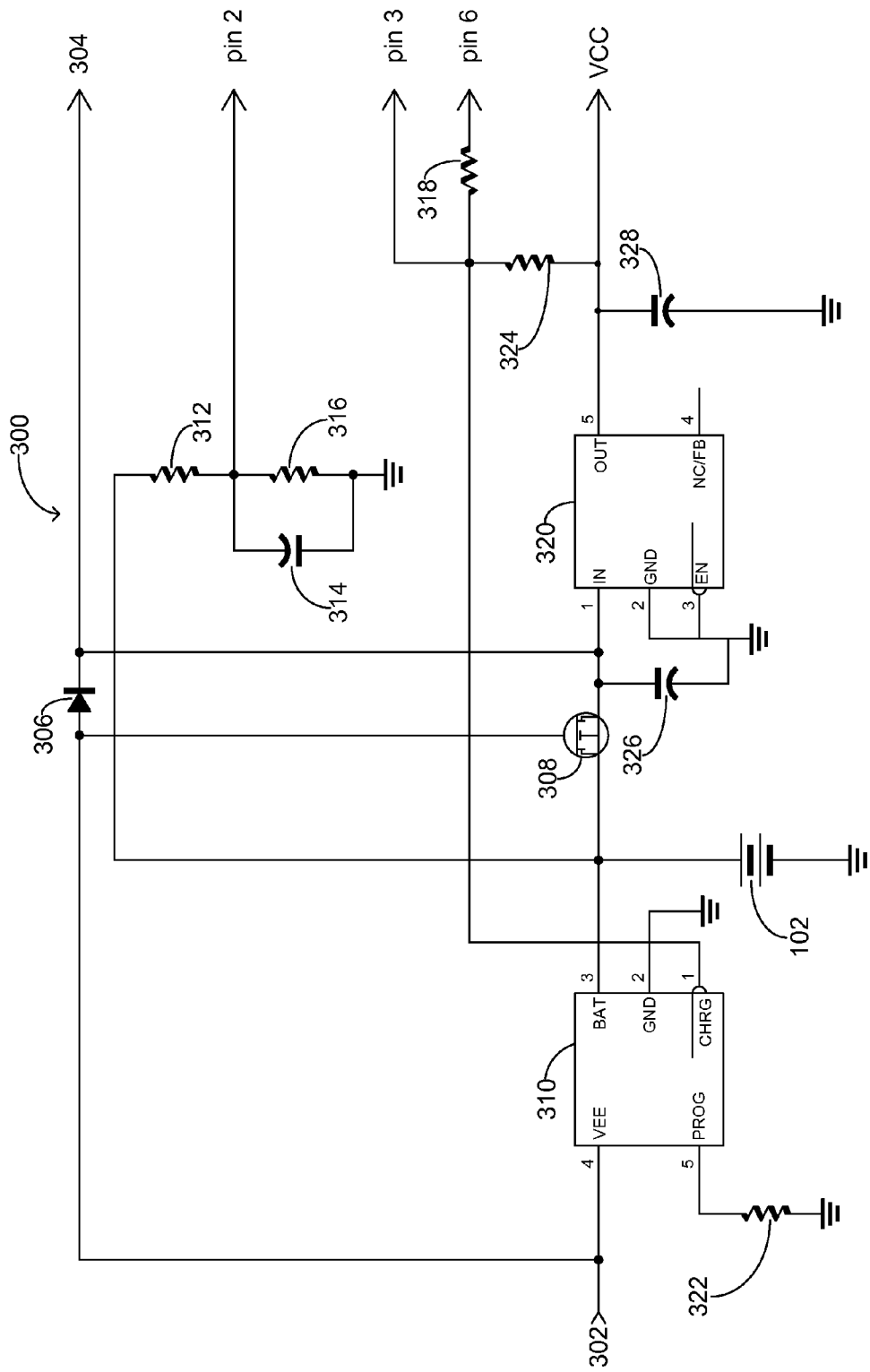
FIG. 13 is a circuit diagram showing a battery charging circuit according to an example embodiment.

FIG. 13 is a circuit diagram showing a battery charging circuit 300 according to an example embodiment. The battery charging circuit 300 may include, for example, a voltage source 302 coupled to a motor input 304 via a diode 306. The voltage source 302 may include, for example, the output node 256 shown in FIG. 12. The diode 306 may be coupled to the motor 104 (not shown in FIG. 13) and to the voltage source 302. The diode 306 may allow current to flow from the voltage source 302 to the motor 104. The motor input 304 may provide power to the motor 104. The motor 104 may spin a disk (shown in FIG. 16D) upon which a plurality of magnets are mounted, according to an example embodiment.

The battery charging circuit 300 may also include the rechargeable battery 102. The rechargeable battery 102 may, for example, include a lithium ion battery. The battery charging circuit 300 may recharge the rechargeable battery 102 with the voltage source 302, and may enable the rechargeable battery 102 to supply power to the motor 104, such as when a voltage of the voltage source 302 drops below a threshold voltage level, according to an example embodiment.

The battery charging circuit 300 may include a metal-oxide-semiconductor field-effect transistor (MOSFET) 308. The MOSFET 308 may include a gate coupled to the voltage source 302 and a source-drain channel coupled to the rechargeable battery 102. For example, a source or a drain of the MOSFET 308 may be coupled to the rechargeable battery 102.

According to an example embodiment, the MOSFET 308 may include a p-channel MOSFET which allows current to flow from the rechargeable battery 102 through the MOSFET 308 to the motor input 304 only when a voltage level of the voltage source 302 drops below a threshold voltage value. In this example, the MOSFET 308 may allow the voltage source 302, but not the rechargeable battery 102, to supply power to the motor 104 via the motor input 304 when the voltage level of the voltage source 302 exceeds the threshold voltage value. However, when the voltage level of the voltage source 302 drops below the threshold voltage value, the rechargeable battery 102 may supply power to the motor 104 via the motor input 304. The diode 306, which may include a Schottky diode, may prevent current from flowing from the rechargeable battery 102 back to the voltage source 302.

In an example embodiment, the battery recharging circuit 300 may include a battery charger 310. The battery charger 310 may include a supply voltage pin (VEE) coupled to the voltage source 302, and a battery pin (BAT) coupled to the rechargeable battery 102. The battery charger 310 may, for example, include a single cell lithium-ion battery charger using a constant-current/constant voltage algorithm. The battery charger 310 may deliver 400 milliamperes of charge current with a final float voltage accuracy of ±1%. The battery charger 310 may include an internal p-channel MOSFET and thermal regulation circuitry.

According to an example embodiment, the battery charging circuit 300 may include a microprocessor 108 (not shown in FIG. 13). The microprocessor 108 may control the motor 104, and may include a voltage monitor pin (pin 2) which receives a signal from the rechargeable battery 102. The voltage monitor pin may be coupled to the rechargeable battery 102 via a first resistor 312, for example. The voltage monitor pin and first resistor 312 may be grounded via a first capacitor 314 and second resistor 316 connected in parallel, according to an example embodiment.

The first resistor 312 may, for example, have a resistance of about one megaohm. The second resistor 316 may, for example, have a resistance of about 100 kiloohms. The first capacitor 314 may, for example, have a capacitance of about 0.1 microfarads.

The microprocessor 108 may also include at least one charging monitor pin which receives a signal from a charge pin (CHRG) of the battery charger 310. The microprocessor 108 may, for example, include a pin 3 which is directly coupled to the charge pin of the battery charger 108, and a pin 6 which is coupled to the charge pin of the battery charger 108 via a third resistor 318. The third resistor 318 may, for example, have a resistance of about 2.49 kiloohms.

In an example embodiment, the battery charging circuit 300 may include a voltage regulator 320. The voltage regulator 320 may, for example, regulate the voltage of the rechargeable battery 102 and supply a regulated voltage VCC to the microprocessor 108. The regulated voltage VCC may, for example, be approximately 3.3 volts. The voltage regulator 320 may, for example, include a TPS77033 low-dropout voltage regulator with low dropout voltage, ultra-low power operation, and miniaturized packaging. A bypass capacitor 326, which may have a capacitance of about 0.1 microfarads, may improve transient response and noise rejection. An output capacitor 328, which may have a capacitance of about ten microfarads, may stabilize the internal control loop of the voltage regulator 320.

In an example embodiment, the battery charging circuit 300 may begin a charge cycle when a voltage at the voltage source 302 rises above an under voltage lock out (UVLO) threshold level with a fourth resistor 322 (which may, for example, have a resistance of about 2.49 kiloohms) coupled between a programming pin (PROG) of the battery charger 310 and ground, or when a battery is coupled to the charger output (CHRG) of the battery charger 310. If at battery pin (BAT) of the battery charger 310 falls below a threshold voltage level, such as approximately 2.9 volts, the battery charger may enter a trickle charge mode. In the trickle charge mode, the battery charger 310 may emit a current, such as approximately 40 milliamperes or ⅒ of a programmed charge current, from the charger output to bring the voltage of the rechargeable battery 102 to a safe level for full current charging. If the battery pin voltage rises above the threshold voltage level such as approximately 2.9 volts, the battery charger 310 may enter a constant-current mode, and may emit a current, such as 400 milliamperes or the programmed charge current, from the charger output to the rechargeable battery. If the battery pin reaches a final float voltage, such as 4.2 volts, the battery charger 310 may enter a constant-voltage mode and reduce the current emitted from the charger output. The charge cycle may end when the current drops below a threshold value, such as 40 milliamperes or ⅒ of the programmed value. At the end of the charge cycle, the battery charger 310 may stop providing any current through the battery pin.

The charge current may be programmed for the programmed value, such as 400 milliamperes, using the fourth resistor 322 between the programming pin to ground. The fourth resistor 322 may, for example, have a resistance of 2.49 kiloohms to set the programmed charge current at 400 milliamperes.

The battery charger 310 may detect the end of the charge cycle, such as by using an internal, filtered comparator to monitor the programming pin. The battery charger 310 may terminate charging when a voltage value of the programming pin falls below a threshold for a specified period of time, such as below 100 millivolts for one millisecond. In response to detecting the end of the charge cycle, the battery charger 310 may enter a standby mode and latch off the charge current. In the standby mode, the battery charger 310 may monitor the voltage level of the battery pin. If the voltage of the battery pin drops below a recharge threshold, such as approximately 4.05 volts, the battery charger 310 may begin another charge cycle and supply current to the rechargeable battery 102. The battery charger 310 may also begin another recharge cycle in response to the magnetic field being removed and reapplied to the secondary coil 252, such as when the charging probe (shown in FIG. 16B) is removed and reinserted.

In an example embodiment, the charger output of the battery charger 310 may have three states: a strong pull-down state, a weak pull-down state, and a high impedance state. In the strong pull-down state, a relatively large current, such as approximately twenty milliamperes, may flow out of the charger output. The strong pull-down state may indicate that the battery charger is in a charge cycle. Once the charge cycle has ended, the state of the charger output may be determined by undervoltage lockout conditions.

In the weak pull-down state, a relatively small current, such as approximately two milliamperes, may flow out of the charger output. The weak pull-down may indicate that the voltage source 302 meets the UVLO conditions and the battery charger 310 is ready to charge. The high impedance state, with no current flowing out of the charging output, may indicate that the battery charger 310 is in UVLO mode, because either the voltage source 302 is less than a threshold voltage, such as 100 millivolts, above the battery pin voltage, or insufficient voltage is applied to the voltage source 302.

In an example embodiment, the microprocessor 108 (not shown in FIG. 13) may distinguish between the strong pull-down, weak pull-down, and high impedance modes. The microprocessor 108 may, for example, detect the strong pull-down state indicating that the battery charger 310 is in a charge cycle by forcing a digital output pin 6 into a high impedance state and measuring a voltage at pin 3. An N-channel MOSFET (not shown), which may be included in the battery charger 310, may pull the charge pin low despite the voltage at the third resistor 318.

When the charge cycle has terminated and the charger output of the battery charger 310 is in the weak pull-down state, emitting the relatively small current, such as approximately two milliamperes, the voltage of the pin 3 may be pulled high by the third resistor 318. The microprocessor 108 may determine if there is a relatively small current indicating the weak pull-down state by, for example, forcing the digital output pin 6 into a low impedance state. The relatively high current may pull the pin 3 low through a fifth resistor 324, which may have a resistance of, for example, about one megaohm.

The microprocessor 108 may determine that the charger output is in the high impedance mode, indicating that the battery charger 310 is in UVLO mode, based on the pin 6 being pulled into a high impedance state and measuring the voltage on pin 3.

The microprocessor 108 may monitor the voltage of the rechargeable battery 102, such as via pin 2. Monitoring the voltage of the rechargeable battery 102 may allow the microprocessor 108 to determine the energy capacity of the rechargeable battery 102. The first resistor 312 and second resistor 316 may form a voltage divider network. The voltage divider network may scale the voltage to acceptable limits of the pin 2 of the microprocessor 108. The first capacitor 314 may act as a bypass capacitor. The microprocessor 108 may, for example, measure the voltage at pin 2 and multiply by the ratio of the first resistor 312 to the second resistor 316 to determine the voltage of the rechargeable battery 102.

In an example embodiment, a housing (shown in FIG. 16A) may enclose the voltage source 302, the diode 306, the rechargeable battery 102, and the motor 104. The housing may be disk-shaped, may include no electrical contacts on an outside surface of the housing, and/or may be waterproof.

Figure 14:
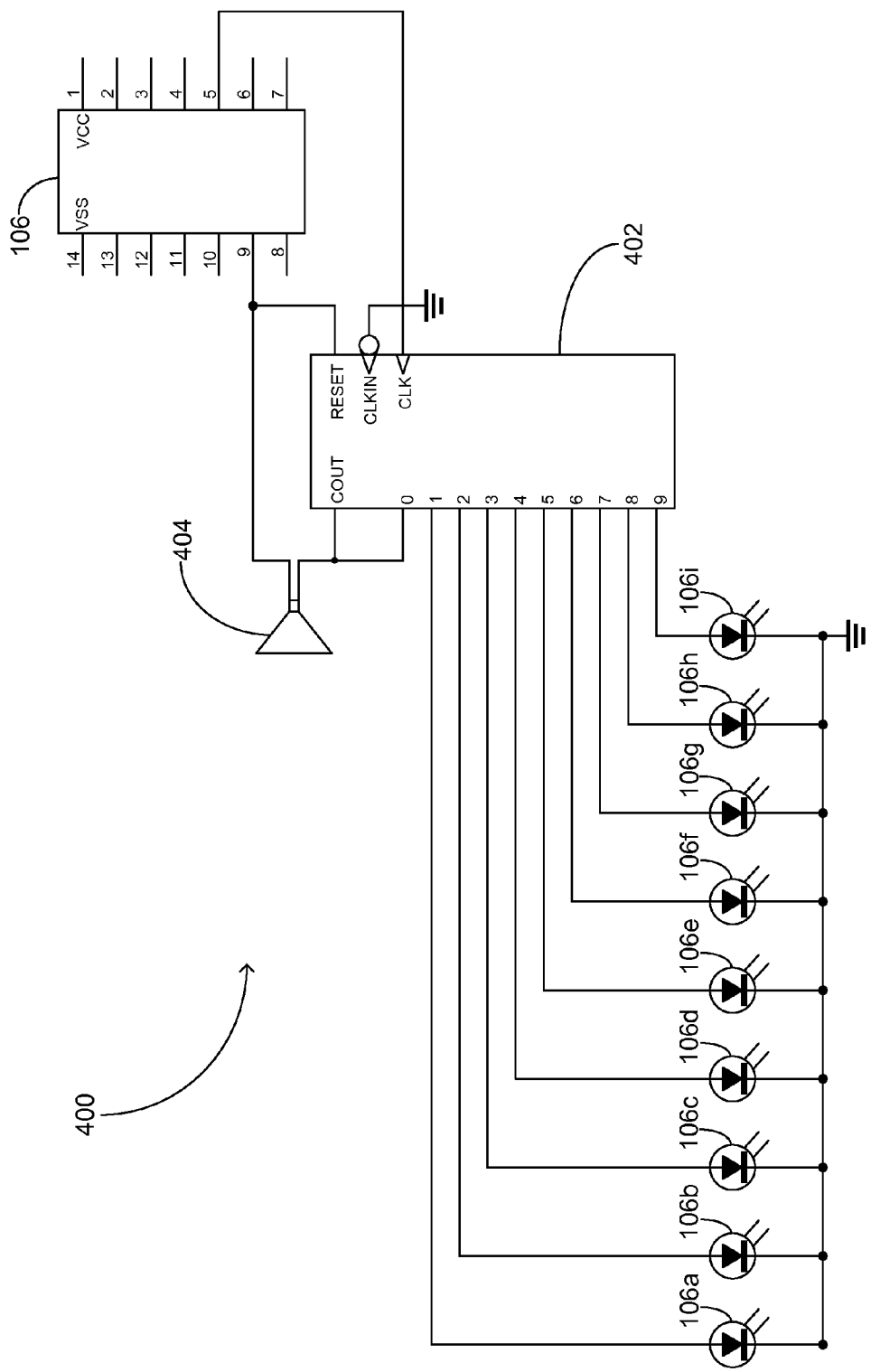
FIG. 14 is a circuit diagram showing a visual indicating circuit according to an example embodiment.

FIG. 14 is a circuit diagram showing the visual indicating circuit 400 according to an example embodiment. The visual indicating circuit 400 may include the microprocessor 108 and a plurality of visual indicators 106a, 106b, 106c, 106d, 106e, 106f, 106g, 106h, 106i. The plurality of visual indicators 106a, 106b, 106c, 106d, 106e, 106f, 106g, 106h, 106i may, for example, include a plurality of light-emitting diodes (LESs). While nine visual indicators 106a, 106b, 106c, 106d, 106e, 106f, 106g, 106h, 106i are shown in FIG. 14, the visual indicating circuit 400 may include any number of visual indicators.

The microprocessor 108 may monitor the voltage level of the rechargeable battery 102 (not shown in FIG. 14) and light a number of the plurality of visual indicators 106a, 106b, 106c, 106d, 106e, 106f, 106g, 106h, 106i. The number may, for example, be based on the monitored voltage level. For example, if the rechargeable battery 102 is fully charged, all of the plurality of visual indicators 106a, 106b, 106c, 106d, 106e, 106f, 106g, 106h, 106i may be turned on; if the rechargeable battery 102 is less than fully charged, then a proportionate number of the plurality of visual indicators 106a, 106b, 106c, 106d, 106e, 106f, 106g, 106h, 106i may be turned on. The microprocessor 108 may turn on the number of the plurality of visual indicators 106a, 106b, 106c, 106d, 106e, 106f, 106g, 106h, 106i by turning the number of the plurality of visual indicators 106a, 106b, 106c, 106d, 106e, 106f, 106g, 106h, 106i on and off at a frequency that is imperceptible to a human eye, according to an example embodiment.

While not shown in FIG. 14, the visual indicating circuit 400 may also include the motor 104 which spins the disk upon which is mounted the plurality of magnets. As shown in FIG. 16D, the plurality of magnets may be mounted onto the disk in a circular pattern with alternating polarities. The microprocessor 108 may, for example, cause the motor 104 to spin the disk for a predetermined time duration. While the motor 104 is spinning the disk, the microprocessor 108 may light all of the plurality of visual indicators 106a, 106b, 106c, 106d, 106e, 106f, 106g, 106h, 106i in a rotational sequence, according to an example embodiment. The microprocessor may light all of the plurality of visual indicators 106a, 106b, 106c, 106d, 106e, 106f, 106g, 106h, 106i in the rotational sequence by, for example, periodically providing clock pulses to the counter 402. A frequency of the lighting the plurality of visual indicators 106a, 106b, 106c, 106d, 106e, 106f, 106g, 106h, 106i in the rotational sequence may increase during an end portion of the predetermined time duration. The increase in the frequency may alert a user that the therapy cycle is almost over.

While also not shown in FIG. 14, the visual indicating circuit 400 may also include the rechargeable battery 102 which supplies power to the motor 104. The rechargeable battery 102 may also supply power to the microprocessor 108, such as via the voltage regulator 320 (not shown in FIG. 14). According to an example embodiment, the microprocessor 108 may cause the motor 104 to spin the disk upon determining that an outside power source (such as the magnetic field induced by the charging probe circuit 200) has been removed from the visual indicating circuit 400 and/or the rechargeable battery 202, and/or upon determining that the voltage level of the rechargeable battery 102 exceeds a threshold voltage level and.

The microprocessor 108 may, for example, light the plurality of visual indicators 106a, 106b, 106c, 106d, 106e, 106f, 106g, 106h, 106i via a counter 402. The counter 402 may, for example, include a CD74HC 4017 decade counter clocked by the microprocessor 108. The counter 402 may include a high-speed silicon gate complimentary metal-oxide semiconductor (CMOS) five-stage Johnson counter with ten decoded outputs. The outputs may normally remain low, and sequentially transition from low to high at the low to high transitions of the clock input (CLK).

The microprocessor 108 may light the plurality of visual indicators 106a, 106b, 106c, 106d, 106e, 106f, 106g, 106h, 106i via the counter 402 by, for example, periodically providing a number of clock pulses and a reset pulse to the counter 402. For example, the microprocessor 108 may sequentially provide a number of clock pulses to the counter 402 equal to the number of the plurality of visual indicators 106a, 106b, 106c, 106d, 106e, 106f, 106g, 106h, 106i which are to light or turn on, and then provide the reset pulse to the counter 402. After providing the reset pulse to the counter 402, the microprocessor 108 may provide the number of clock pulses to the counter 402 and then the reset pulse, and so on. The microprocessor 108 may provide the clock pulses by providing inputs to a clock pin (CLK) of the counter 402, and may provide the reset pulses by providing inputs to a reset pin (RESET) of the counter 402, according to an example embodiment.

According to an example embodiment, the visual indicating circuit 400 may include an audible output element 404. The audible output element 404 may, for example, include a piezoelectric horn capable of producing high frequency beeps, and may be driven by the counter 402. The microprocessor 108 may, for example, cause the audible output element 404 to periodically emit an audible output, such as a beep, when the motor 104 is spinning.

The visual indicating circuit 400 may be included in a housing (shown in FIG. 16A). The housing may enclose the motor 104, the disk, the rechargeable battery 102, and the microprocessor 108. The plurality of visual indicators 106a, 106b, 106c, 106d, 106e, 106f, 106g, 106h, 106i may be mounted in the housing. The housing may be disk-shaped, include no electrical contacts on an outside surface of the housing, and/or may be waterproof.

FIG. 15 is a circuit diagram showing the tachometer circuit 500 according to an example embodiment. The tachometer circuit 500 may include, for example, a power source or motor input 304 which supplies power to the motor 104. The power source may, for example, include the rechargeable battery 102. The tachometer circuit 500 may also include the motor 104. The motor 104, which may include a direct current (DC) motor, may control a disk 502 upon which a plurality of magnets 504 may be mounted. The magnets 504 may, for example, be mounted onto the disk 502 in a circular manner with alternating polarities.

The tachometer circuit 500 may also include the tachometer 110. The tachometer 110 may, for example, include a Melexis US4881, which may include a bipolar Hall-effect switch designed with mixed signal CMOS technology. The tachometer 110 may integrate a voltage regulator, Hall sensor with a dynamic offset cancellation system, a Schmitt trigger, and an open-drain output driver. The power to operate the tachometer 110, which may have a voltage of 3.3 volts in an example embodiment, may be provided by the microprocessor 108, which in turn may be powered by the regulated voltage VCC.

The tachometer 110 may monitor a magnetic field generated by the plurality of magnets 504 and provide a signal to the microprocessor 108 based on the monitored magnetic field. The magnetic coupling of the tachometer 110 to the magnetic field generated by the magnets 504 spinning around the motor 104 is shown by the dashed line in FIG. 15. The tachometer 110 may, for example, monitor a frequency of magnetic flux generated by the plurality of magnets 504 and provide the signal to the microprocessor 108 based on the frequency of magnetic flux. The signal may, for example, include a pulse for each change of magnetic flux, or pulses with a frequency proportional to the speed of rotation of the disk 502.

A resistor 506, which may have a resistance of ten kiloohms in an example embodiment, may cause the signal output by the tachometer 110 to have a voltage value between zero and the regulated voltage VCC, and may be about 3.3 volts in an example embodiment. A filter capacitor 508, which may have a capacitance of 0.001 microfarads in an example embodiment, may filter out noise and stabilize the detected magnetic frequency.

The magnetic frequency generated by the magnets 504 may be a function of the number of poles and the rotation speed of the disk 502. In an example in which the disk 502 includes ten poles (ten magnets 504 with alternating polarities N-S-N-S-N-S-N-S-N-S), one complete rotation by the disk 502 may generate five sinusoidal magnetic cycles. The motor 104 may generate a prescribed frequency of, for example, 100 magnetic cycles per second (CPS) by rotating the disk 502 twenty rotations per second (20 rotations per second×5 sinusoidal magnetic cycles per rotation=100 cycles per second).

The tachometer circuit 500 may also include a microprocessor, which may be the same microprocessor 108 included in the visual indicating circuit 400. A capacitor 510, which may have a capacitance of 0.15 microfarads in an example embodiment, may reduce high frequency noise on the regulated voltage VCC. The microprocessor 108 may control the motor 104 based on the signal received from the tachometer 110. The microprocessor 108 may, for example, control the motor 104 based on the signal by comparing the signal to a reference signal. In an example embodiment, the microprocessor 108 may cause the motor 104 to increase or decrease the speed of rotation of the disk 502 and magnets 504 to maintain a desired strength of the magnetic field.

The microprocessor 108 may control the motor 104 by controlling a current flowing through the motor 104. The motor 104 may, for example, include a precision DC motor with gold brushes. For example, if the microprocessor 108 determines, based on the signal received from the tachometer 110, that the frequency of magnetic flux is too low, the microprocessor 108 may increase the speed of rotation of the disk 502 by allowing current to flow through the motor 104. Or, if the microprocessor 108 determines that the frequency of magnetic flux is too high, the microprocessor may decrease the speed of rotation of the disk 502 by not allowing current to flow through the motor 104. The microprocessor 108 may control the motor 104 by applying an input to a transistor 506 which is connected in series with the motor 104. The input may, for example, take the form of pulse width modulation (PWM). Applying the input to the transistor 506 may vary a resistance of the transistor 506 and thereby vary the power available to the motor 104 to spin the disk 502. The transistor 506 may, for example, include a metal-oxide-semiconductor field-effect transistor (MOSFET); in this example, the microprocessor 108 may control the motor 104 by controlling a voltage applied to a gate of the MOSFET. A diode 512 may allow any reverse-biased voltage to dissipate without causing the motor 104 to reverse direction.

The tachometer circuit 500 may, for example, be included in a housing (shown in FIG. 16A). The housing may, for example, enclose the power source or motor input 304, the motor 104, the disk 502, the tachometer 110, and the microprocessor 108. The housing may be disk-shaped, have no electrical contacts on an outside surface of the house, and/or may be waterproof.

Figure 15B:
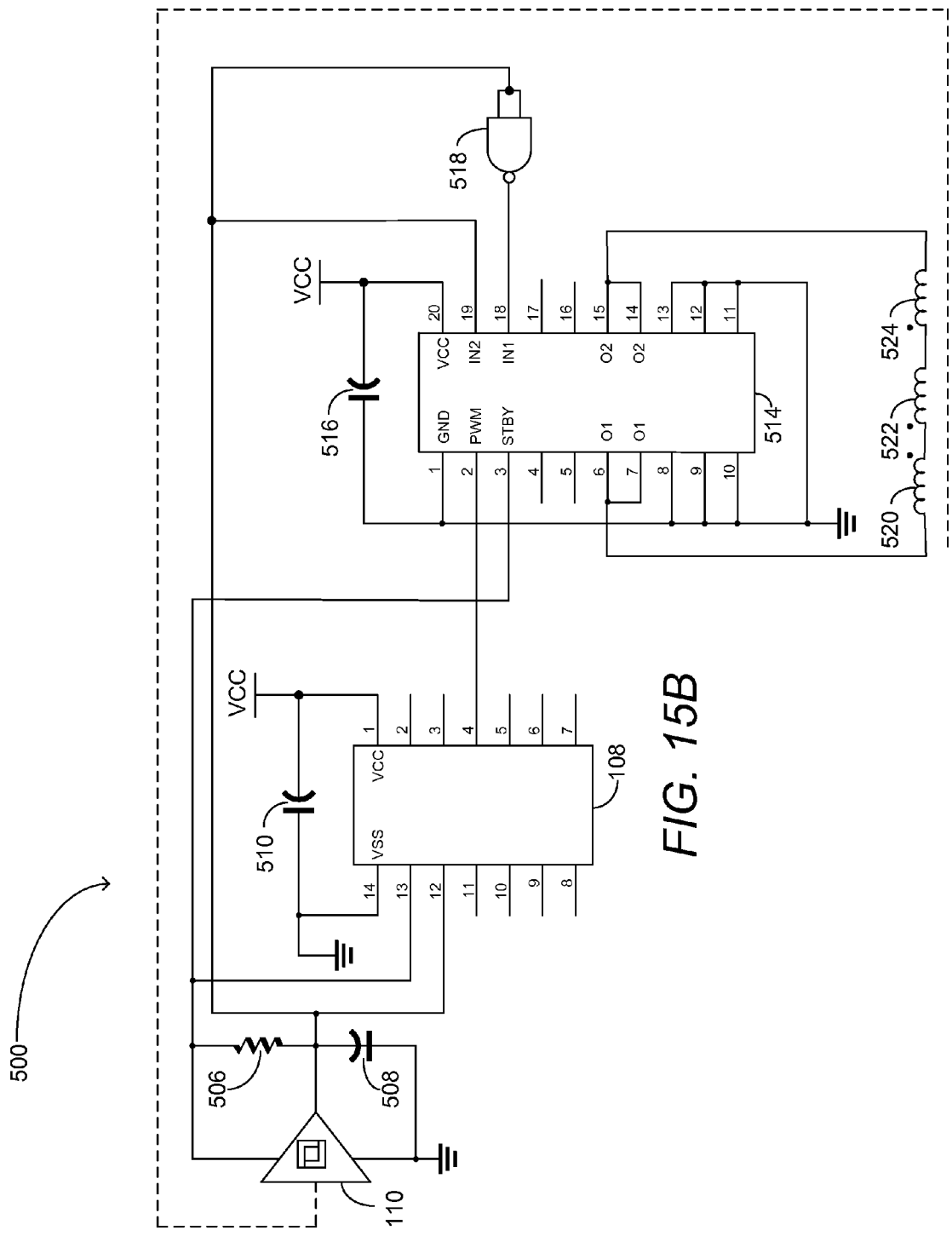
FIG. 15B is a circuit diagram showing a tachometer circuit according to an example embodiment using a brushless motor.

FIG. 15B is a circuit diagram showing a tachometer circuit 500 according to an example embodiment using a brushless motor. The brushless motor may include a rotor extending from a center of the disk 502 in a direction perpendicular to a plane of the disk, a stator made up of inductive coils, a commutator, which may be the tachometer 110 or Hall-effect switch, and a driver, which may include a driver integrated circuit 514. In this example, the microprocessor 108 may provide a control signal to the driver integrated circuit 514. The brushless motor design may be smaller than the motor design described above with reference to FIG. 15A. The driver integrated circuit 514 may, for example, include a Toshiba TB6593FNG. The control signal may be a pulse width modulation signal. The microprocessor 108 may, for example, provide the control signal and/or pulse width modulation signal to a pulse width modulation pin of the driver integrated circuit 514. The driver integrated circuit 514 may also receive a standby signal from the tachometer 110 as a standby signal input pin of the driver integrated circuit 514.

The driver integrated circuit 514 may also receive power at a small signal supply (VCC) pin of the driver integrated circuit 514. The driver integrated circuit 514 may also have a plurality of pins coupled to ground. The tachometer circuit 500 may include a capacitor 516 coupled between the VCC pin and the ground to mediate any spikes in the power supply.

The tachometer 110 may also provide one or more signals to the driver integrated circuit 514. The tachometer 110 may provide a signal to the driver integrated circuit 518 at a control input 1 (IN1) pin and/or a signal to a control input 2 (IN2) pin of the driver integrated circuit 518. The signals to the respective control input pins may be provided from different pins of the tachometer 110. The tachometer 110 may, for example, provide the signal to the IN1 pin of the driver integrated circuit 514 via a NAND gate 518 or via a NOT gate, according to example embodiments.

The driver integrated circuit 514 may provide a current to a plurality of inductive coils 520, 522, 524 based on the control signal and/or the signal received from the tachometer 110. In the example shown in FIG. 15B, the tachometer circuit 500 may include three inductive coils 520, 522, 524. However, the tachometer circuit 500 may include other numbers of inductive coils 520, 522, 524, according to example embodiments. The current provided to the inductive coils 520, 522, 524 by the driver integrated circuit 514 may create a rotating magnetic field which drives the magnets 504 on the disk 502, causing the disk 502 to spin. The microprocessor 108 may be programmed to control the speed of the disk 502 using the control signal and/or pulse width modulation signal, such as described above with reference to FIG. 15A. The driver integrated circuit 514 may alternately reverse the current flowing through the inductive coils 520, 522, 524 to generate the appropriate magnetic field to drive the alternately polar magnets. The tachometer 110, which may include the Hall-effect switch, may set timing for when to reverse polarity or current direction on the inductive coils 520, 522, 524.

The inductive coils 520, 522, 524 may be wound on a portion of a ferrite pot core, such as around about half of a ferrite port core. The inductive coils 520, 522, 524 may include at least 100 turns of wire, such as 111 turns; the wire may, for example, be of sixe 30 American Wire Gauge (AWG).

Figure 15C:
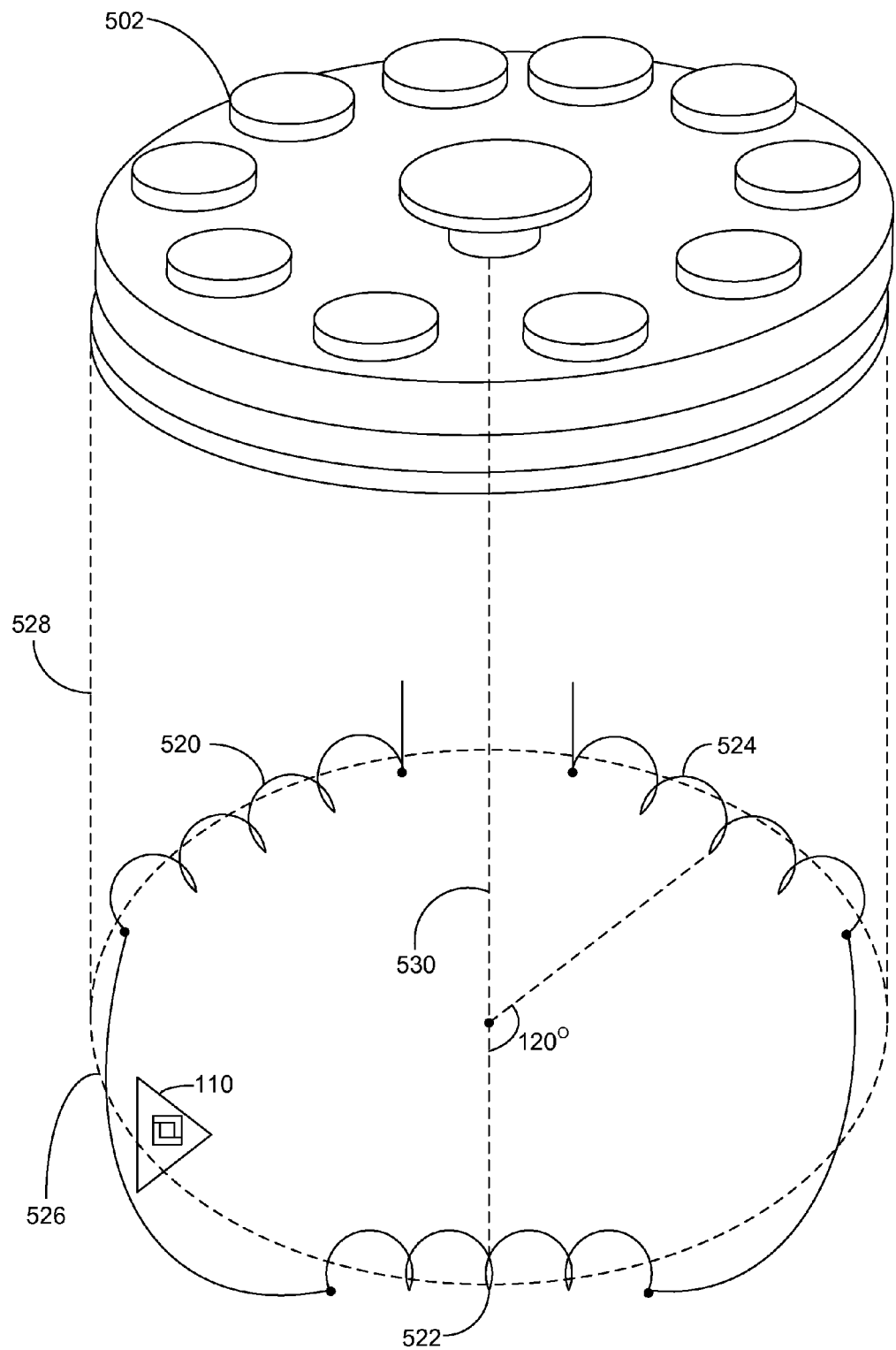
FIG. 15C is a diagram showing the disk, a tachometer, and inductive coils according to an example embodiment using the brushless motor.

FIG. 15C is a diagram showing the disk 502, the tachometer 110, and inductive coils 520, 522, 524 according to an example embodiment using the brushless motor. The inductive coils 520, 522, 524 may lie along an imaginary circle 526. The inductive coils 520, 522, 524 may, for example, be equally spaced along the imaginary circle 526. In the example in which the tachometer circuit 500 includes three inductive coils 520, 522, 524, the inductive coils 520, 522, 524 may be spaced 120 degrees apart along the imaginary circle 526. The imaginary circle 526 may, for example, be parallel to a plane of the disk 502. A center 528 of the imaginary circle 526 may lie along an imaginary line 530 extending from a center of the disk 502; the imaginary line 530 may extend from the center of the disk, and may be perpendicular to a plane of the disk 502. A rotor extending from the disk 502 may, for example, extend along the imaginary line 530 into the housing 602 (shown in FIG. 16A). The imaginary circle 526 may, for example, be considered one end of a cylinder 532, with the opposite end of the cylinder 532 formed by the disk 502. The location of the inductive coils 520, 522, 524 along the imaginary circle 526 may assure self-starting by preventing the magnets 504 and/or the disk 502 from coming to rest on a torque minima location.

The tachometer 110 may lie along the imaginary circle 526. The tachometer 110 may, for example, be located about halfway between two of the coils 520, 522. The location of the tachometer 110 between two of the coils 520, 522 may allow the tachometer 110 to provide accurate timing signals to the microprocessor 108 and/or driver integrated circuit 514 to alternate the direction of the current through the coils 520, 522, 524, generating the correct magnetic fields to drive the alternating magnets 504 and the disk.

FIG. 16A is an illustration of a magnetic therapy device 600 according to an example embodiment. The magnetic therapy device 600 may, for example, include a housing 602. The housing 602 may be disk-shaped, such as approximately the size of a hockey puck. The housing 602 may, for example, have a five inch diameter and be two inches thick. The housing 602 may include a Velcro strip (not shown), enabling a user to secure the magnetic therapy device to his or her body. The housing 602 may have not electrical contacts on an outside surface of the housing 602, according to an example embodiment. The housing 602 may be waterproof. The housing 602 may include an aperture 604.

The magnetic therapy device 600 may include the current inducing circuit 250 (not shown in FIG. 16A). The current inducing circuit 250 may be mounted onto an inside surface (not shown) of the housing 602.

The current inducing circuit 250 may convert a magnetic field into a direct current (DC) voltage. In an example embodiment, the current inducing circuit 250 may include the secondary coil 252. The secondary coil 252 may induce a current from the magnetic field. The secondary coil 252 may surround the aperture 604. The current inducing circuit 250 may also include the delay switch 254 and the output node 256. The delay switch 254 may be coupled to the secondary coil 252, and the output node 256 may be coupled to the delay switch 254 and to the battery charging circuit 300.

The magnetic therapy device 600 may also include the battery charging circuit 300 (not shown in FIG. 16A). The battery charging circuit 300 may be enclosed by the housing 602. The battery charging circuit 300 may charge the rechargeable battery 102 based on the DC voltage. The battery charging circuit 300 may also, based on the rechargeable battery 102, supply power to the motor 104 and to the microprocessor 108.

The magnetic therapy device 600 may also include the microprocessor 108 (not shown in FIG. 16A). The microprocessor 108 may be enclosed by the housing 602. The microprocessor 108 may control the plurality of visual indicators 106a, 106b, 106c, 106d, 106e, 106f, 106g, 106h, 106i. The microprocessor 108 may also control the motor 104. The microprocessor 108 may, for example, be programmed so that each therapy cycle of the magnetic therapy device 600, in which the motor 104 spins the disk 502 with the plurality of magnets 504, lasts approximately twenty minutes. The rechargeable battery 102 may, when fully charged, have enough energy to power twenty such therapy cycles, according to an example embodiment.

The magnetic therapy device 600 may also include the plurality of visual indicators 106a, 106b, 106c, 106d, 106e, 106f, 106g, 106h, 106i. The plurality of visual indicators 106a, 106b, 106c, 106d, 106e, 106f, 106g, 106h, 106i may be mounted onto the housing 602, and may emit light outside the magnetic therapy device 600. While nine visual indicators 106a, 106b, 106c, 106d, 106e, 106f, 106g, 106h, 106i are shown, the magnetic therapy device 600 may include any number of visual indicators 106a, 106b, 106c, 106d, 106e, 106f, 106g, 106h, 106i. The visual indicators 106a, 106b, 106c, 106d, 106e, 106f, 106g, 106h, 106i may indicate both the charge state of the rechargeable battery 102 and the progress of a therapy cycle.

The magnetic therapy device 600 may also include the motor 104 (not shown in FIG. 16A). The motor 104 may generate a magnetic field by spinning the disk 502 upon which the plurality of magnets 504 are mounted.

Figure 16B:
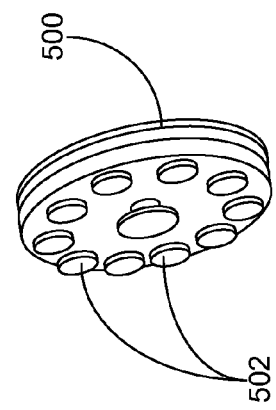
FIG. 16B is an illustration of a charging probe according to an example embodiment.

FIG. 16B is an illustration of a charging probe 606 according to an example embodiment. The charging probe 606 may include the charging probe circuit 200 (not shown in FIG. 16B). The primary coil 208 may, for example, be included in a probe 608 which fits into the aperture 604 of the housing 602. The AC input 202 may, for example, be included in an electrical power cord 610 which may plug into an electrical outlet to receive AC power. The electrical power cord 610 may, for example, receive power from sources between about 85 and 275 volts AC and/or 47 to 63 Hertz, allowing the charging probe 606 to charge the magnetic therapy device 600 from many electrical outlets.

Figure 16C:
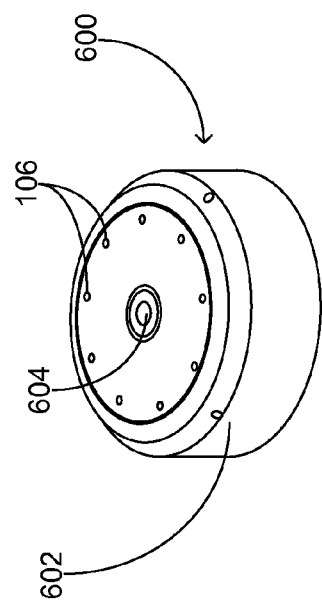
FIG. 16C is an illustration of the magnetic therapy device with the charging probe inserted according to an example embodiment.
Figure 16D:
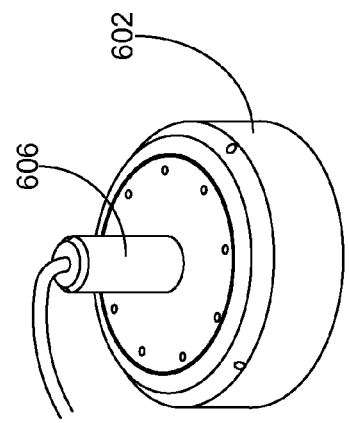
FIG. 16D is an illustration of a disk with a plurality of magnets according to an example embodiment.

FIG. 16C is an illustration of the magnetic therapy device 600 with the charging probe 606 inserted according to an example embodiment. The charging probe 606 may, in the inserted position, supply power to the magnetic therapy device 600 with no electrical contacts.

FIG. 16D is an illustration of the disk 502 with the plurality of magnets 504 according to an example embodiment. The magnets 504 may be mounted onto the disk 502 in a circular pattern with alternating polarities.

The magnetic therapy device 600 may, in an example embodiment, be self-contained, needing no outside components or inputs except the charging probe 606. The magnetic therapy device 600 may be waterproof and/or water submersible, enabling a person to use the magnetic therapy device 600 in a bathtub, for example. The magnetic therapy device may also be cleaned with soap and water, for example.

The magnetic therapy device 600 may also have no electrical contacts and rely completely on the rechargeable battery 102, which may be magnetically coupled to the charging probe 606, for power. The transfer of energy from the charging probe 606 to the magnetic therapy device 606 by the magnetic field may make the magnetic therapy device safe from electrical shock hazards. The magnetic therapy device 600 may have no switches, push buttons, or other such controls other than the charging probe 606.

Processors suitable for the execution of a computer program include, by way of example, both general and special purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in special purpose logic circuitry.

Implementations may be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of such back-end, middleware, or front-end components. Components may be interconnected by any form or medium of digital data communication, e.g., a communication network. Examples of communication networks include a local area network (LAN) and a wide area network (WAN), e.g., the Internet.

While certain features of the described implementations have been illustrated as described herein, many modifications, substitutions, changes and equivalents will now occur to those skilled in the art. It is, therefore, to be understood that the appended claims are intended to cover all such modifications and changes as fall within the true spirit of the embodiments of the invention.

What is claimed is:

1. A magnetic therapy device comprising:
   a housing;
   a disk comprising a plurality of magnets thereon, the disk being mounted inside the housing and configured to rotate within the housing;
   a tachometer configured to monitor a magnetic field generated by the plurality of magnets and provide a frequency signal to a microprocessor based on the monitored magnetic field;
   the microprocessor configured to provide a control signal to a driver integrated circuit based on the frequency signal, the microprocessor being programmed to provide the control signal to maintain a constant speed of rotation of the disk based on the frequency signal;
   the driver integrated circuit configured to provide a current to a plurality of coils based on the control signal; and the plurality of coils configured to generate, based on the current received from the driver integrated circuit, a magnetic field which will generate a force on the plurality of magnets and thereby cause the disk to rotate.

2. The magnetic therapy device of claim 1, wherein the housing is disk-shaped.

3. The magnetic therapy device of claim 1, wherein the housing encloses the disk, the tachometer, the microprocessor, the driver integrated circuit, and the plurality of coils.

4. The magnetic therapy device of claim 1, wherein the housing encloses the disk, the tachometer, the microprocessor, the driver integrated circuit, and the plurality of coils, and the housing includes no electrical contacts on an outside surface of the housing.

5. The magnetic therapy device of claim 1, wherein the plurality of magnets are mounted onto the disk in a circular manner with alternating polarities.

6. The magnetic therapy device of claim 1, wherein the tachometer is configured to monitor a frequency of magnetic flux generated by the plurality of magnets and provide the frequency signal to the microprocessor based on the frequency of magnetic flux.

7. The magnetic therapy device of claim 1, wherein the tachometer is configured to monitor a frequency of magnetic flux generated by the plurality of magnets and provide the frequency signal to the microprocessor based on the frequency of magnetic flux, the frequency signal including a pulse for each change of magnetic flux.

8. The magnetic therapy device of claim 1, wherein the tachometer is configured to monitor a frequency of magnetic flux generated by the plurality of magnets and provide the frequency signal to the microprocessor based on the frequency of magnetic flux, the frequency signal including pulses with a frequency proportional to a speed of rotation of the disk.

9. The magnetic therapy device of claim 1, wherein the tachometer includes a Hall-effect switch.

10. The magnetic therapy device of claim 1, wherein:
the tachometer is configured to provide the frequency signal to the driver integrated circuit; and
the driver integrated circuit is configured to provide the current to the plurality of coils based on the control signal and the frequency signal.

11. The magnetic therapy device of claim 1, wherein the tachometer is located about halfway between two of the coils.

12. The magnetic therapy device of claim 1, wherein the microprocessor is configured to provide the control signal to the driver integrated circuit, the control signal including a pulse width modulation signal.

13. The magnetic therapy device of claim 1, wherein the microprocessor is configured to provide the control signal to the driver integrated circuit based at least in part on comparing to the frequency signal to a reference signal.

14. The magnetic therapy device of claim 1, wherein the driver integrated circuit is configured to provide the current to the plurality of coils, an amplitude of the current being based on the control signal.

15. The magnetic therapy device of claim 1, wherein the plurality of coils includes three coils 120 degrees apart around a center of the disk.

16. The magnetic therapy device of claim 1, wherein:
the plurality of magnets are mounted onto the disk along an imaginary circle with alternating polarities; and
the plurality of coils includes three coils 120 degrees apart along an imaginary cylinder, the imaginary cylinder passing through the imaginary circle in a direction perpendicular to a plane of the disk.

17. The magnetic therapy device of claim 1, wherein the plurality of coils are each wound around at least a portion of a ferrite pot core.

18. The magnetic therapy device of claim 1, wherein each of the plurality of coils includes at least 100 turns.

* * * * *